(12) United States Patent
Schlegel et al.

(10) Patent No.: US 10,189,157 B2
(45) Date of Patent: Jan. 29, 2019

(54) MANIPULATING SYSTEM AND MANIPULATING APPARATUS FOR SURGICAL INSTRUMENTS

(71) Applicant: Karl Storz SE & Co. KG, Tuttlingen (DE)

(72) Inventors: Sebastian Schlegel, Berlin (DE); Bastian Blase, Berlin (DE)

(73) Assignee: Karl Storz SE & Co. KG, Tuttlingen (DE)

(*) Notice: Subject to any disclaimer, the term of this patent is extended or adjusted under 35 U.S.C. 154(b) by 0 days.

(21) Appl. No.: 15/261,127

(22) Filed: Sep. 9, 2016

(65) Prior Publication Data

US 2017/0072561 A1    Mar. 16, 2017

(30) Foreign Application Priority Data

Sep. 15, 2015    (DE) .................. 10 2015 115 559

(51) Int. Cl.
*B25J 9/10*    (2006.01)
*A61B 34/00*    (2016.01)
(Continued)

(52) U.S. Cl.
CPC ....... *B25J 9/1035* (2013.01); *A61B 17/07207* (2013.01); *A61B 34/70* (2016.02);
(Continued)

(58) Field of Classification Search
CPC .. B25J 9/1035; A61B 34/70; A61B 17/07207; A61B 2017/00473; A61B 2017/00477; F16H 1/22
See application file for complete search history.

(56) References Cited

U.S. PATENT DOCUMENTS

2011/0277775 A1* 11/2011 Holop ................ A61B 17/3423
                                                     128/849
2011/0282356 A1    11/2011 Solomon et al.
(Continued)

FOREIGN PATENT DOCUMENTS

DE    102012008537 A1    10/2013
EP        2889009 A2     7/2015
WO        9639944 A1    12/1996

OTHER PUBLICATIONS

German Search Report Application No. DE 10 2015 115 559.1 dated Jun. 6, 2016 10 pages.
(Continued)

*Primary Examiner* — Zakaria Elahmadi
(74) *Attorney, Agent, or Firm* — Whitmyer IP Group LLC

(57) ABSTRACT

A minimally invasive manipulating system and a manipulating apparatus for instruments are disclosed. The apparatus comprises a frame and at least one instrument carrier including a holding section for an instrument arm. The instrument carrier is movably mounted to the frame and arranged to be coupled with at least one drive. The instrument carrier is at least sectionally rotatable about its longitudinal axis. The holding section comprises a driving interface that involves at least one transmission port. An instrument drive is assigned to the transmission port. The instrument carrier comprises a transmission section in which at least one transmission element is arranged that is configured for motion transmission between the instrument drive and the transmission port. The at least one transmission element is arranged concentrically with respect to the longitudinal axis. The transmission port is arranged off-center with respect to the longitudinal axis.

22 Claims, 13 Drawing Sheets

(51) Int. Cl.
*F16H 1/22* (2006.01)
*A61B 17/072* (2006.01)
*A61B 17/00* (2006.01)

(52) U.S. Cl.
CPC ...... *F16H 1/22* (2013.01); *A61B 2017/00473* (2013.01); *A61B 2017/00477* (2013.01); *Y10S 901/25* (2013.01)

(56) References Cited

U.S. PATENT DOCUMENTS

| | | | |
|---|---|---|---|
| 2014/0001234 A1* | 1/2014 | Shelton, IV | A61B 17/07207 227/176.1 |
| 2014/0236174 A1* | 8/2014 | Williams | A61B 17/00234 606/130 |
| 2014/0305995 A1* | 10/2014 | Shelton, IV | A61B 17/07207 227/180.1 |
| 2014/0309666 A1* | 10/2014 | Shelton, IV | A61B 17/068 606/139 |
| 2015/0032151 A1* | 1/2015 | Ishida | A61B 17/2909 606/205 |
| 2015/0119918 A1 | 4/2015 | Blase et al. | |
| 2015/0196313 A1* | 7/2015 | Ishida | A61B 17/29 606/205 |
| 2016/0249945 A1* | 9/2016 | Shelton, IV | A61B 17/068 606/171 |

OTHER PUBLICATIONS

European Search Report Application No. 16187605.7 Completed: Apr. 6, 2017; dated Apr. 19, 2017 9 pages.

\* cited by examiner

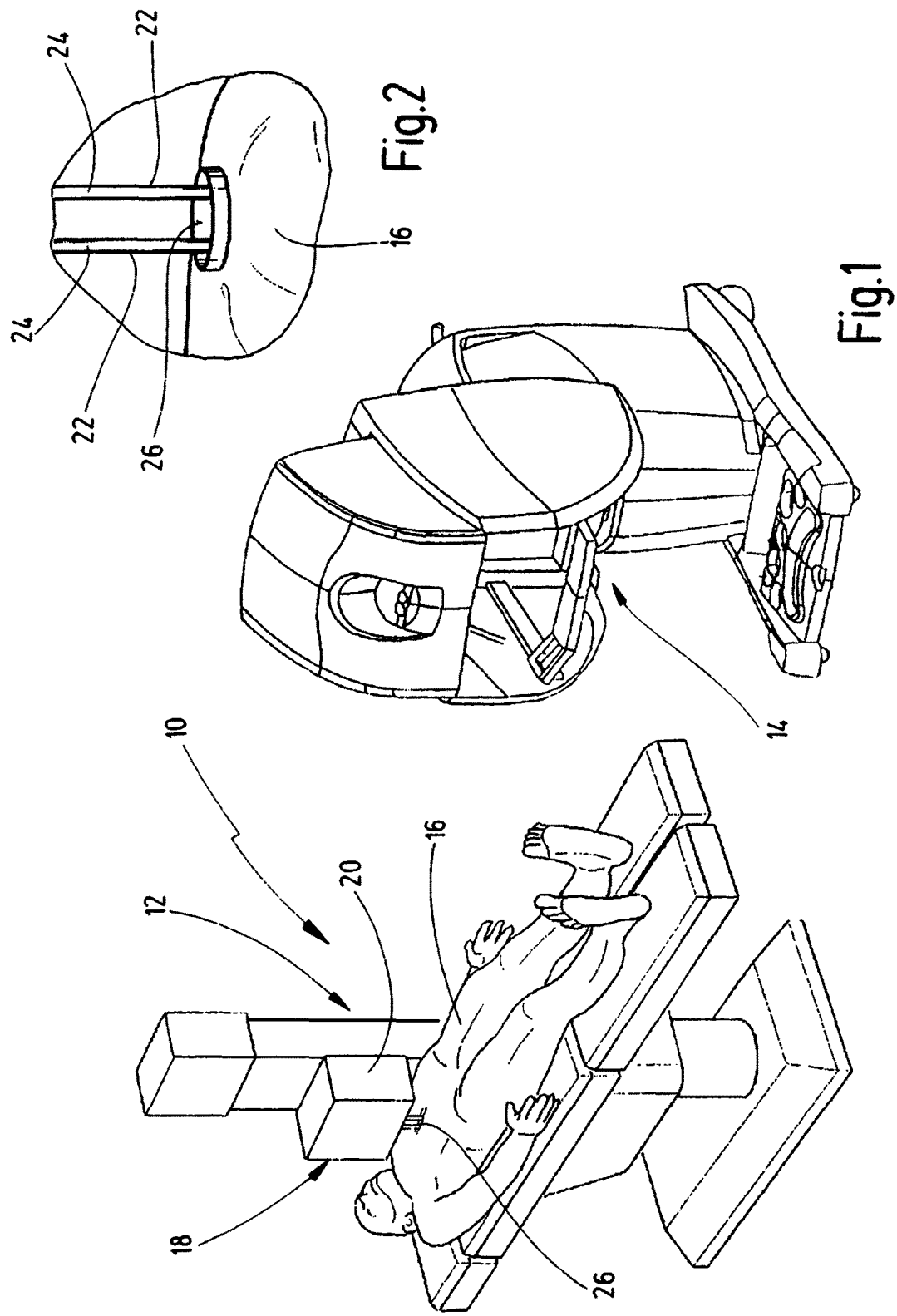

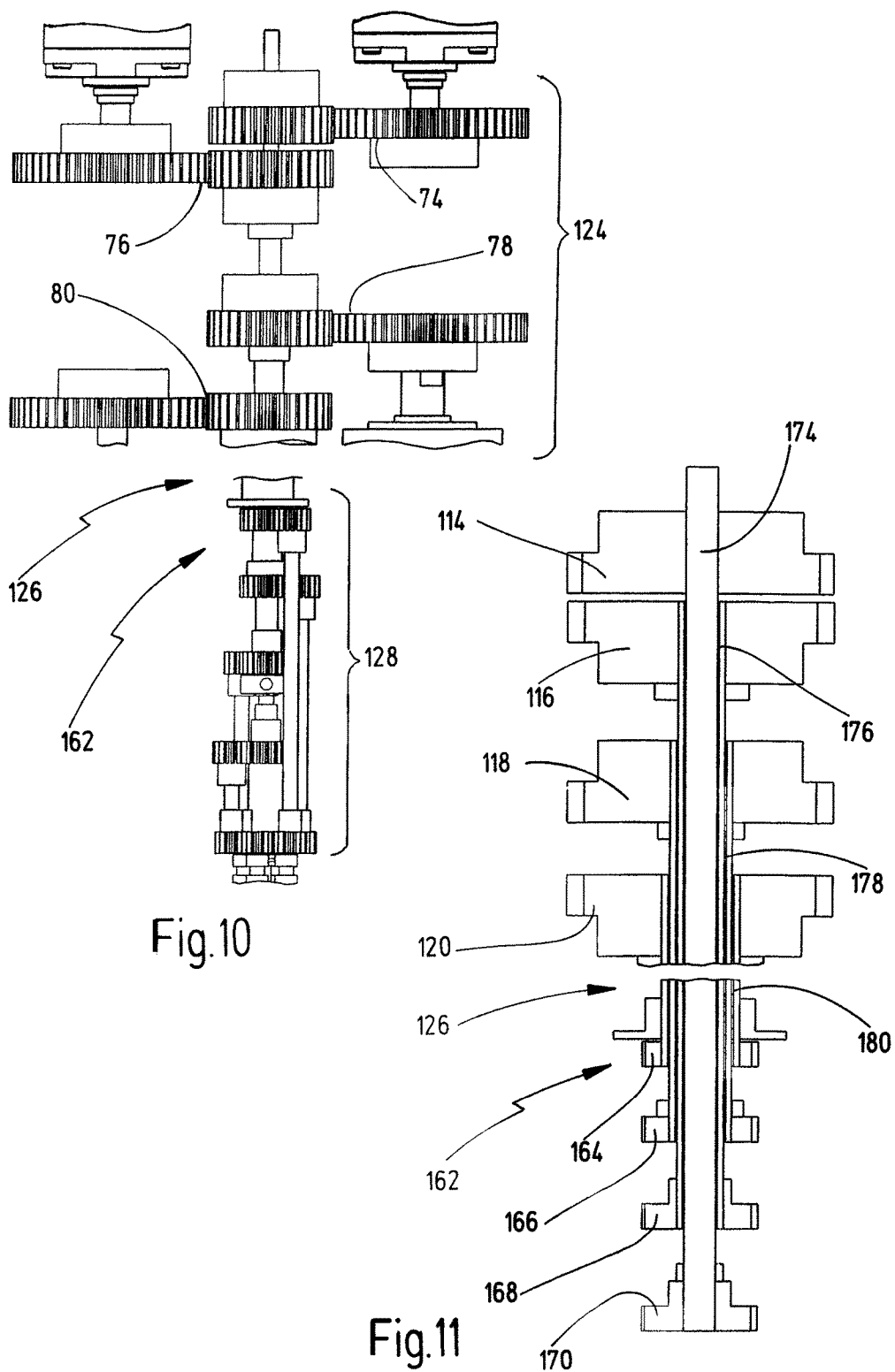

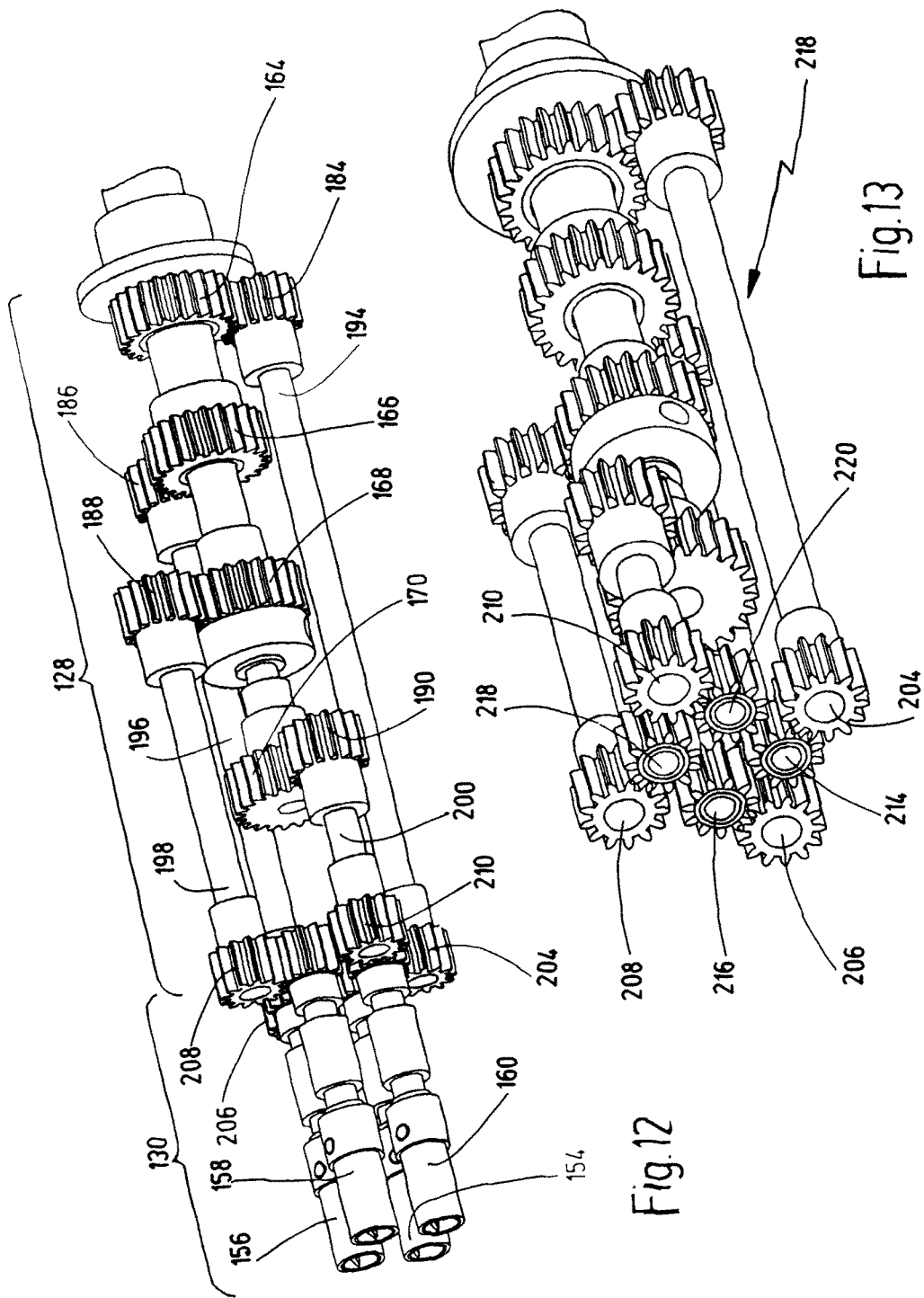

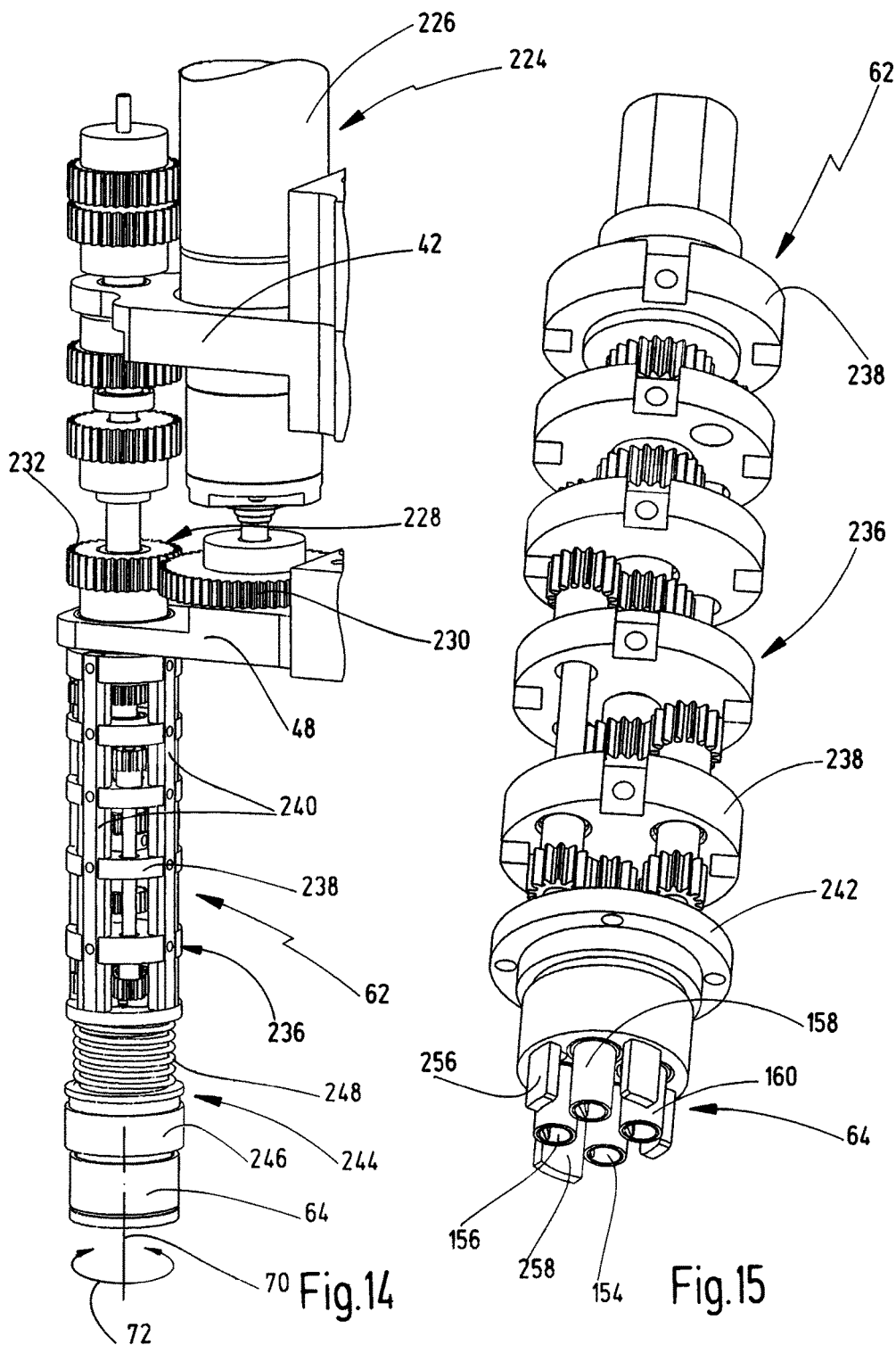

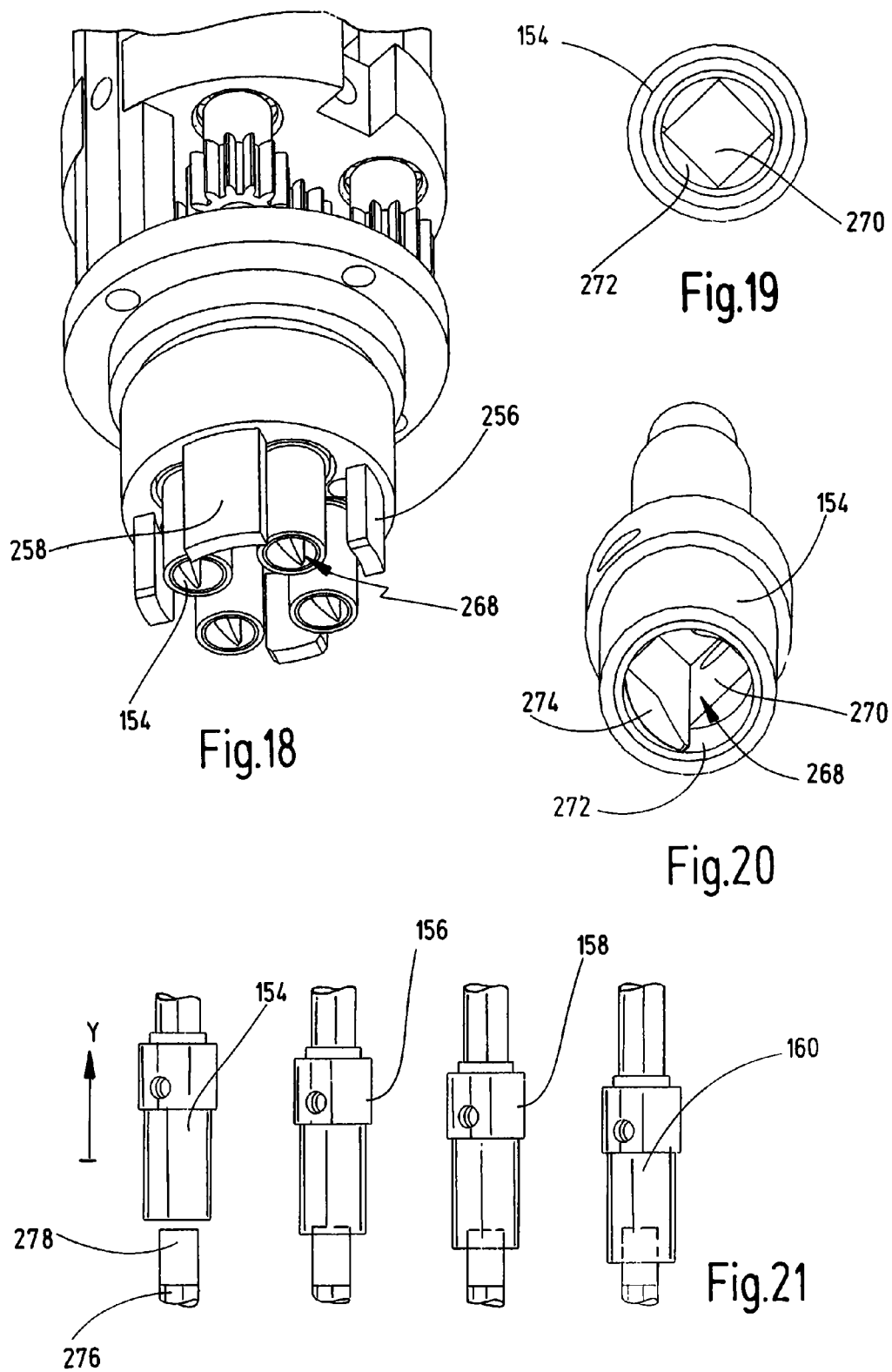

MANIPULATING SYSTEM AND MANIPULATING APPARATUS FOR SURGICAL INSTRUMENTS

CROSS-REFERENCES TO RELATED APPLICATIONS

This application claims priority from German patent application 10 2015 115 559.1, filed on Sep. 15, 2015. The entire content of that priority application is fully incorporated by reference herewith.

BACKGROUND

The present disclosure relates to a manipulating apparatus for holding and handling instruments for minimally invasive procedures, comprising a frame and at least one instrument carrier comprising a holding section for holding an instrument arm. The disclosure further relates to a manipulating system for minimally invasive surgical operations and further procedures. In exemplary embodiments, the disclosure further relates to a remote manipulating system for minimally invasive single-port-operations, comprising a control platform that is provided with such a manipulating apparatus.

More generally, the present disclosure relates to the field of minimally invasive surgery and the field of robotic operation systems and/or the field of robotic remote operation systems. For minimally invasive procedures, surgeons generally use natural body openings or artificially created body openings so as to insert several instruments into the interior of the body of a to-be-treated person and/or a to-be-treated animal. Minimally invasive procedures may involve procedures of therapeutic nature, procedures of diagnostic nature and combinations thereof. It is generally desired to use access openings to the body that are small as possible so as to minimize the stress to the patient as much as possible. Frequently, instruments for minimally invasive procedures enable only limited movements and/or operations in the interior of the body.

WO 96/39944 A1 discloses a surgical instrument manipulator, comprising an affixable carrier base, an instrument holder that is movably arranged at the carrier base and adapted to hold a surgical instrument in a releasable fashion, a driving arrangement, and a coupling device, wherein the instrument holder comprises a body and an instrument carrier that is movably attached to the body and provided with an interface which is arranged to be coupled with the surgical instrument so as to attach the instrument to the instrument holder in a releasable fashion, wherein the driving arrangement is operatively coupled with the instrument holder so as to provide the instrument with at least two degrees of freedom including a rotation of the surgical instrument with respect to the carrier base and an axial movement of the surgical instrument with respect to the carrier base, wherein the driving arrangement comprises a first controllable and/or steerable motor that is operatively connected with the instrument carrier so as to move the same, and a second steerable and/or controllable motor that is operatively connected with the body of the instrument holder so as to move the same with respect to the carrier base, wherein the coupling device is arranged for releasably mounting the instrument holder to the carrier base and the driving arrangement, and wherein the instrument holder is removable from the carrier base and the driving arrangement for sterilization.

For quite some time now, systems for robotic operations, for instance in the field of remote medicine, are at the stage of research and testing. In the past, generally an approach was pursued that involved an adaption of known functional principles from the field of (industrial) robotics and/or industrial production, assembly and handling to the field of medical technology. Approaches of that kind, however hit limits when particular requirements in the field of minimally invasive surgery are addressed.

Surgical instruments for minimally invasive procedures typically comprise an elongated shape at a very small diameter. Nevertheless, there is also a need for instruments which may perform extended functions in the interior of the body. This may for instance involve a pivotability about at least one pivot axis and the actuation of surgical tools which are arranged at the distal end of the instruments. A common diameter of instruments for minimally invasive procedures is for instance 10 mm (millimeter). This installation space restriction poses high requirements to mechanical, optical and electronic components for such instruments.

Frequently, a plurality of instruments is used in a minimally invasive procedure. This may also take place in a simultaneous fashion. In other words, often two or even more instruments are simultaneously inserted in the interior of the patient. By way of example, this may involve a simultaneous use of an endoscopic instrument for monitoring and a surgical instrument for the procedure as such.

Further, so-called single-port-operations and multi-port-operations are known. With single-port-operations, the procedure is performed at merely one opening in the body. With multi-port-operations, a plurality of body openings is used. It is generally desired to use as few body openings as possible so as to minimize the stress for the patient. However, when two or more instruments are simultaneously inserted in the interior of the body of the patient, and when this takes place about merely a single access, the installation space restrictions are even further increased. Known manipulators or robots for medical applications may then reach their limits. This is sometimes attributable to the fact that the instruments that are to be inserted in a simultaneous fashion may (outside of the body) be simply not guided in a fashion sufficiently close to one another and/or oriented with respect to one another to be inserted in the interior of the body in a parallel fashion, for instance.

Medical instruments for operative procedures which are arranged to be pivoted about more than one axis are for instance known from US 2015/0119918 A1. In this way, the freedom of movement in the interior of the body can be remarkably increased. Generally, there is a need for instruments including an increased number of degrees of freedom. The degrees of freedom may for instance relate to degrees of freedom of movement (longitudinal movements, pivot movements, rotations). Degrees of freedom may, however, also relate to the actuation of surgical tools (scissors, forceps, etc.) which are again attributable to movements. The more the degrees of freedom are implemented in an instrument, the more paths for motion transmission and/or for transmission of forces and/or torques have to be considered. In a shaft of an instrument or an arm of an instrument, movements generally may be transmitted by pull/push or by rotation movements. The more complex the instrument is arranged and the more degrees of freedom are present, the more complex and sluggish is the operation of the instrument. Hence, motor-supported or motor-aided manipulating systems for surgical procedures may be an option also in cases when the aspect of remote medicine is not or not exclusively addressed.

Medical manipulating systems for instruments having a plurality of degrees of freedom (for instance two, three or four degrees of freedom in the instrument itself) may significantly facilitate the operation of the instrument, as a purely mechanical actuation is on the one hand exhausting and on the other hand very challenging in terms of coordination. Accordingly, a workplace may be provided for the operating surgeon that includes respective input elements, for instance joysticks, dummy-instruments and/or phantom instruments and such like. In this way, the operating surgeon may create movement signals which may be converted by a control device of the manipulating system into control signals for drives that in turn convert those signals into movements.

In view of this, it is an object of the present disclosure to present a manipulating apparatus for surgical instruments and a manipulating system comprising such a manipulating apparatus.

It is a further object of the present disclosure to present a manipulating apparatus for surgical instruments and a manipulating system comprising such a manipulating apparatus that are suitable for surgical instruments or medical instruments having an enhanced functional scope.

It is a further object of the present disclosure to present a manipulating apparatus for surgical instruments that is suited for instruments that provide an increased number of (mechanical) degrees of freedom and/or degrees of freedom of movement.

It is a further object of the present disclosure to present a manipulating apparatus that is suited for single-port-operations.

It is a further object of the present disclosure to present a manipulating apparatus that is suited for the simultaneous use of at least two instruments that are simultaneously inserted in the body of a to-be-treated patient.

It is a further object of the present disclosure to present a manipulating apparatus that further increases the functional scope of the instrument, for instance by providing at least a further (movement) degree of freedom.

It is a further object of the present disclosure to present a manipulating apparatus that enables a simple instruments change.

It is a further object of the present disclosure to present a manipulating apparatus that, when in operation, contributes to a reproducible and predictable behavior of the instruments during the operations.

It is a further object of the present disclosure to present a manipulating apparatus that contributes to a high absolute positioning accuracy and a high relative positioning accuracy and repeatability of the instruments.

SUMMARY

In regard of the manipulating apparatus, these and other objects of the invention are achieved by a manipulating apparatus for holding and handling instruments for minimally invasive procedures, the manipulating apparatus comprising a frame and at least one instrument carrier including a holding section for holding an instrument arm, wherein the instrument carrier is movably mounted at the frame and arranged, for movement thereof, to be coupled with at least one drive, wherein the instrument carrier is at least sectionally rotatable about its longitudinal axis, wherein the holding section comprises a driving interface for transmitting mechanical energy to the instrument arm, wherein the driving interface involves at least one transmission port for motion transmission, for instance for torque transmission, wherein an instrument drive is assigned to the transmission port, wherein the instrument carrier, at least sectionally along its longitudinal extension, comprises a transmission section in which at least one transmission element is arranged which enables a motion transmission between the instrument drive and the transmission port, wherein the at least one transmission element is oriented in a fashion concentrically with respect to the longitudinal axis of the instrument carrier, and wherein the transmission port is arranged in an off-center fashion with respect to the longitudinal axis.

In accordance with the invention, the manipulating apparatus namely simply permits the transmission of a driving impulse (for instance a driving torque) to an instrument which is mounted at the instrument carrier, even though the instrument carrier and an instrument that is mounted thereon are jointly rotatable with respect to the frame about the longitudinal axis of the instrument carrier. In this way, the manipulating apparatus may on the one hand provide a further degree of freedom of movement, namely a (global) rotation of the instrument about the longitudinal axis thereof. However, within the instrument arm the desired movements may be transmitted without an adverse effect on the (global) rotatability of the instrument. The instrument arm may be generally also referred to as instrument shaft. The instrument arm typically comprises a longitudinal extension which amounts to a multiple or even many times the diameter.

As used herein, a freedom of movement degree provided by the manipulating apparatus for the instrument involves that a respective drive train is provided at the manipulating apparatus that is operable to actuate a function (e.g., a driving feature and/or effector feature, etc.) of the instrument, when the instrument is mounted.

In certain exemplary embodiments, the manipulating apparatus is suited for instruments in which the drive for at least one degree of freedom of movement, preferably for two or more degrees of freedom of movement, is performed in the instrument by torque transmission. In other words, for these degrees of freedom in the instrument, no push rods are required for transmission from the manipulating apparatus to the instrument. In an exemplary embodiment, the transmission of a torque, for instance by torsion bars, flexible or rigid shafts and such like is an option when the instrument comprises at least one, preferably a plurality of pivotable section(s) so that at least one, preferably two or more of the degrees of freedom of movement is a rotatory degree of freedom (and/or pivoting degree of freedom). A mere actuation by push rods would possibly involve a feedback during a movement about an axis which induce a movement of another axis which is not desirable. Drawbacks of that kind may be reduced or even eliminated by design measures. However, this involves particularly huge efforts.

The at least one transmission port that transmits the torque to the instrument is arranged in an off-center fashion with respect to the longitudinal axis of the instrument carrier. Accordingly, the transmission port as such is pivoted about the longitudinal axis of the instrument carrier when the instrument carrier is rotated. This does not necessarily have to involve a rotation of the transmission port about its (own) longitudinal axis. Preferably, the at least one transmission element is coupled with the transmission port in such a way that the transmission port is also moved at the same magnitude and in the same direction when the instrument carrier is rotated about the longitudinal axis.

Preferably, the motion transmission at and/or in the instrument carrier involves low backlash and/or is nearly backlash-free. This may for instance involve motion transmission via sufficiently rigid and/or stiff elements, i.e. not via flexible elements (for instance compensation clutches, flexible shafts, wire cables and such like). Rather, it is preferred that gear stages are used for the motion transmission at the manipulating apparatus, wherein the gear stages are coupled with one another by stiff shafts or tubes. This may overall contribute to an increased accuracy of the operation of the instrument.

Generally, the instrument carrier is arranged to receive the instrument and to transmit driving torques for actuating the instrument at the distal end of the instrument carrier to the proximal end of the instrument shaft. This involves that required drives (instrument drives) for the degrees of freedom of the instrument may be arranged in a fashion spaced away from the proximal end of the instrument shaft or arm at the manipulating apparatus as the instrument carrier bridges a distance space between the drives and the instrument.

Preferably the instrument comprises two, three or four (internal) degrees of freedom of movement which may for instance involve pivot movements and actuations of tools and such like. Preferably, the manipulating apparatus provides, in a mediate fashion via the instrument carrier, at least two further (global) degrees of freedom of movement for the instrument, for instance a rotatory degree of freedom about the longitudinal axis (of the instrument carrier) and a push movement along the longitudinal axis and/or parallel to the longitudinal axis. Movements which use these degrees of freedom preferably have no influence on (local) conditions and/or movements of the instruments itself. In other words, preferably a local motion reference of the instrument is independent of a global motion reference, even if the drives for the instrument are at least mediately arranged in a fashion fixed to a frame.

In a preferred refinement of the manipulating apparatus, the driving interface of the at least one instrument carrier comprises at least two, preferably at least three or four, transmission ports, at least two of which are arranged in a fashion radially displaced from the longitudinal axis and spaced from one another, wherein at least two, preferably at least three or four, transmission elements are arranged in the transmission section which are assigned to the at least two transmission ports, wherein at least two, preferably three or four, instrument drives are provided, wherein the manipulating apparatus provides a first degree of freedom of movement for a mounted instrument to which a first instrument drive, a first transmission element and a first transmission port are assigned, which are coupled with one another for rotation transmission, for instance by gear stages, wherein the manipulating apparatus provides a second degree of freedom of movement for a mounted instrument to which a second instrument drive, a second transmission element and a second transmission port are assigned, which are coupled with one another for rotation transmission, for instance by gear stages, and wherein the first transmission element and the second transmission element are oriented in a fashion concentrically with respect to the longitudinal axis of the instrument carrier and drivable in a fashion independently of one another, wherein the second transmission element is arranged in a tubular fashion and at least sectionally surrounds the first transmission element.

In other words, a plurality of transmission elements for the instrument-sided degrees of freedom of movement is arranged in the transmission section, at least two of which, preferably all transmission elements are oriented in a fashion concentrically with respect to one another. In this way, when a (global) rotation of the instrument arm or shaft during a rotation of the instrument carrier is present, the relative position between the transmission elements is not changed. In some exemplary embodiments, as a result, the instrument drives, particularly the motors thereof that are mediately or directly fixedly attached to the frame, can maintain their position and do not have to be turned or rotated about the longitudinal axis of the instrument shaft when a (global) rotation of the instrument takes place. This enables considerable installation space savings and a remarkable reduction of manufacturing efforts.

In other words, the function of the instrument carrier is similar to a hydraulic rotary union, wherein the instrument carrier, so to say, provides a "mechanical rotary union". The at least sectionally concentrical arrangement of the instrument carrier enables a force transmission and/or torque transmission along a plurality of paths, in fact without undesired interdependencies, interferences and such like between the paths.

According to an exemplary refinement, the manipulating apparatus further provides a third degree of freedom of movement and a fourth degree of freedom of movement for the mounted instrument, wherein a third instrument drive, a third transmission element and a third transmission port are assigned to the third degree of freedom of movement, which are coupled with one another for rotation transmission, for instance by gear stages, wherein a fourth instrument drive, a fourth transmission element and a fourth transmission port are assigned to the fourth degree of freedom of movement, which are coupled with one another for rotation transmission, for instance by gear stages, and wherein the third transmission element and the fourth transmission element are oriented in a fashion concentrically with respect to the longitudinal axis of the instrument carrier and drivable in a fashion independently of one another, wherein the fourth transmission element is arranged in a tubular fashion and at least sectionally surrounds the third transmission element, wherein the third transmission element is arranged in a tubular fashion and at least sectionally surrounds the second transmission element.

Overall, the manipulating apparatus may hence provide five or six degrees of freedom of movement for the instrument. This may involve four (internal) degrees of freedom of movement for the instrument which involve an actuation of the instrument via the four transmission ports. Further, at least two further (global) degrees of freedom of movement may be envisaged, for instance a rotation of the instrument about the longitudinal axis and a translation along the longitudinal axis.

According to a further embodiment, the transmission ports are distributed about a longitudinal axis and arranged in an off-center fashion with respect to the longitudinal axis. This may involve a revolver-like arrangement of the transmission ports. According to an exemplary arrangement, the transmission ports (by means of their respective axes) altogether define a perimeter circle about the longitudinal axis. Similarly, then also the instrument comprises a corresponding number of instrument inputs which are arranged to be coupled with the transmission ports when the instrument is mounted at the instrument carrier. It goes without saying that, for instance, when at the instrument itself a smaller number of degrees of freedom of movement is present than provided by the manipulating apparatus, a reduced number of instrument inputs is provided at the instrument. This is not detrimental as the corresponding degree of freedom of movement on the side of the manipulating apparatus is decoupled from the remaining degrees of freedom of movement.

According to a further embodiment of the manipulating apparatus, the at least one transmission element, preferably each of the transmission elements, is, in the transmission section, arranged in a shaft-like or tubular fashion and coupled with an input-side, proximal gear stage and an output-side, distal gear stage.

Overall, in this way a concentrical arrangement including a plurality of tubes that are mounted in one another may be provided. It goes without saying that the gear stages for the input and output of the transmission elements are axially displaced from the corresponding gear stages of the other transmission elements. The gear wheels of the transmission elements are arranged in a fashion concentrically with respect to the longitudinal axis of the instrument carrier.

According to an exemplary embodiment, the first transmission element is positioned inside and preferably arranged as a solid shaft. The second transmission element is arranged in a tubular fashion and surrounds the first transmission element. The third transmission element is arranged in a tubular fashion and surrounds the second transmission element. The fourth transmission element is arranged in a tubular fashion and surrounds the third transmission element. It goes without saying that also further transmission elements may be envisaged which are arranged in a tubular fashion and which concentrically surround the remaining transmission elements. With the arrangement including four transmission elements, the first (inner) transmission element necessarily comprises the largest axial extension between the proximal gear wheel and the distal gear wheel. With respect to the axial extension between their proximal and distal gear wheels, the second transmission element, the third transmission element and the fourth transmission element are succeeding, wherein the fourth (outer) transmission element comprises the shortest axial extension.

According to a further embodiment, the at least one transmission element is, for torque transmission, at its proximal end, coupled with the instrument drive and, at its distal end, with the transmission port, wherein, when the instrument carrier is rotated about the longitudinal axis, which effects a pivot movement of the transmission port of the same magnitude and in the same direction, the respectively assigned instrument drive remains in its defined relative position with respect to the frame. This may apply for instance to the instrument of the first, second, third and fourth degree of freedom of movement.

According to a further embodiment of the manipulating apparatus, at least one longitudinal guide is formed at the frame which receives a carriage which supports the at least one instrument carrier, wherein the at least one instrument carrier is arranged to be moved together with the carriage with respect to the frame. In this way, a further (fifth) degree of freedom of movement is provided, for instance a translational degree of freedom of movement. At least according to some embodiments, the longitudinal guide is arranged as a vertical guide. It goes without saying that also further orientations of the longitudinal guide may be envisaged. A translational movement of the instrument carrier along the longitudinal guide effects a movement of the mounted instrument having the same magnitude and the same direction.

According to a further embodiment of the manipulating apparatus, the at least one instrument drive, preferably each instrument drive which is assigned to the instrument carrier, is mounted at the carriage. In other words, accordingly, also the instrument drives are displaced together with the instrument carrier when the carriage is longitudinally moved. According to a further embodiment, the instrument drives, provided that a plurality of instrument drives is mounted at the carriage, are arranged in the periphery of the instrument carrier and in a fashion parallel oriented with respect thereto. In an exemplary embodiment, the instrument drives may be at least sectionally arranged in the periphery of the transmission section. This may further reduce the required installation space.

By way of example, also the instrument drives are arranged in a shaft-like or cylindrical fashion and comprise a longitudinal extension which is larger than the diameter. Suitable transmission gears may be attached to the motors. For instance, position-steered and/or position-controlled motors are suited. This may for instance involve so-called servo-motors, for instance brushless DC-servo-motors (direct current servo-motors). Further position-controlled motors may be envisaged. As for each of the instrument-sided degrees of freedom of movement a separate instrument drive is provided, in accordance with an exemplary embodiment, the drives may be oriented parallel with respect to the longitudinal axis and arranged and/or grouped about the instrument carrier. It is advantageous to receive the instrument drives (which may involve the motors thereof) directly at the carriage as in this way short transmission paths are enabled which results in an increased accuracy and in a reduced backlash.

According to an exemplary refinement of this embodiment, the instrument drives are arranged in a fashion about and offset from the instrument carrier at the carriage, wherein the instrument carrier is arranged in a boundary region of the carriage. Preferably, the instrument carrier is arranged at a lateral edge of the carriage. This may contribute to a state where the instrument carrier and the instrument attached thereto may in this direction (laterally) considerably closely approach a desired target position, for instance considerably closely to a further instrument carrier to which a further instrument is mounted. This may further increase the suitability of the manipulating apparatus for single-port-operations.

According to a further refinement, at least two instrument drives are mounted at opposite sides of the carriage. Also in accordance with this embodiment, the instrument drives are oriented in a fashion parallel with respect to the instrument carrier. However, as the instrument carrier itself, due to the concentrical arrangement of the transmission elements, involves a certain longitudinal extension (due to the design thereof), it is possible to arrange and orient the instrument drives in such a way that the longitudinal extension is maximally exploited. This may further contribute to a minimization of the installation space in lateral directions with respect to the longitudinal extension (for instance side directions). Overall, the instrument drives may assume, when four instrument degrees of freedom are used, an H-shaped arrangement with respect to a basis of the carriage.

According to a further embodiment of the manipulating apparatus, the carriage is coupled with a longitudinal drive. Preferably, the longitudinal drive is arranged as a screw drive or ball screw drive. This measure may be further refined such that the longitudinal drive comprises a motor that is mounted in a fashion fixedly attached to a frame, and that drives a spindle. Accordingly, for instance, at the carriage a spindle nut is mounted which is displaced in the longitudinal direction when the spindle is rotated and which moves the carriage. The instrument carrier and an instrument attached thereto are jointly moved with the carriage by the longitudinal drive in the longitudinal direction.

According to a further embodiment of the manipulating apparatus, a rotation drive is arranged at the carriage which effects a rotation of the instrument carrier about its longitudinal axis, wherein the rotation of the instrument carrier effects a rotation entrainment of the least one transmission port about the longitudinal axis. By means of the longitudinal drive, a fifth degree of freedom of movement for the instrument is provided. By means of the rotation drive, a sixth degree of freedom of movement for the instrument is provided. It goes without saying that the manipulating apparatus itself, in at least some embodiments, in turn, may by mounted at a manipulator, robot or a differently shaped (global) movement apparatus.

According to a further embodiment of the manipulating apparatus, the holding section of the at least one instrument carrier comprises a contact interface for transmitting electric energy or electric signals, wherein the contact interface is preferably arranged in a center of the holding section. To this end, for instance a suitable plug or a suitable socket may be provided. Preferably, the contact interface comprises a plurality of contacts. At the instrument side, for instance sensors may be provided, signals of which may be transmitted via the contact interface. It may however be also envisaged that at the instrument side actuators, imagers, arrangements for generating thermal energy and such like are formed. Accordingly, various signals may be transmitted via the contact interface. The contact interface is, when the instrument carrier is rotated, jointly moved with the instrument carrier and the instrument attached thereto. Accordingly, a contact with the frame side of the manipulating apparatus (and/or a higher-lever manipulating system) may be effected via flexible connections, for instance via a cable drag and such like. This may be for instance envisaged when the instrument carrier itself is rotatable about its longitudinal axis only within a defined range. In the alternative, it may also be envisaged to provide slide contacts, ring contacts and such like between the instrument carrier and the frame so as to be able to transmit electric signals and/or electric energy independent of an absolute rotation position of the instrument carrier.

According to a further embodiment of the manipulating apparatus, the holding section of the at least one instrument carrier is formed as a locking receptacle for a proximal end of an instrument, for instance an instrument for minimally invasive surgery or diagnosis, wherein at least one rotational position securing element is formed at the holding section which cooperates in the mounted state with a counter element of an instrument arm so as to effect a defined rotation orientation between the instrument arm and the instrument carrier. The rotational position securing may be effected by suitable protrusions, recesses, toothing and such like. The rotational position securing contributes to the prevention of incorrect assembling. Preferably, the instrument is mounted at the holding section of the instrument carrier in a torque-proof fashion so as to be jointly rotated about the longitudinal axis together with the instrument carrier.

According to a refinement of this embodiment, a plurality of locking elements, for instance of locking balls, is mounted at the holding section which, in the engaged state, engage at least one locking recess at the instrument arm. The locking recess is for instance formed as a circumferential locking groove. However, also embodiments may be envisaged involving a plurality of locking recesses which respectively form recesses that are arranged as spherical segments.

The locking receptacle may further involve an axially displaceable locking sleeve which is mounted at the holding section and arranged to be displaced against a biasing force so as to enable a disengagement of the locking elements from the engaged state. In this way, the instrument arm may be attached to and/or detached from the instrument carrier in a simple and reliable fashion. An unintentional release of the instrument arm is prevented by a biasing force on the locking sleeve. The locking elements are, in an exemplary embodiment, radially displaceable so as to selectively effect a positive-locking position securing between the holding section and the instrument arm. In an exemplary embodiment, the locking sleeve comprises a (flat) cone angle which effects in the engaged state of the instrument arm a self-locking of the locking sleeve and the locking elements.

According to a further embodiment, the manipulating apparatus comprises at least a first instrument carrier and a second instrument carrier that are movably mounted at the frame and which are at least sectionally movable with respect to one another, wherein each instrument carrier is provided with a holding section for holding an instrument arm. In an exemplary embodiment, the instrument carriers are mounted at the frame in a fashion parallel to one another and adjacent to one another. In an exemplary embodiment of the manipulating apparatus, when the instrument carriers are rotated about the longitudinal axis, the instrument drives themselves do not have to be jointly rotated and/or pivoted. This minimizes the required installation space and/or the required movement space. Hence, there exists the option to arrange a plurality of instrument carriers in close proximity, wherein the instrument drives do not or do only marginally increase the achievable minimum distance between the instrument carriers. The suitability of the manipulating apparatus for single-port-operations may be further increased. According to a refinement of this embodiment, the first instrument carrier is mounted to a first carriage and the second instrument carrier is mounted to a second carriage, wherein the first instrument carrier and the second instrument carrier are arranged in facing boundary regions of the carriages, for instance in a fashion immediately adjacent with respect to one another.

According to an exemplary refinement, longitudinal axes of the first instrument carrier and the second instrument carrier are spaced from one another at an offset dimension a which has a relation with respect to an installation space diameter D of the instrument carrier including a ratio (a:D) of less than 3.5:1. In an exemplary embodiment, the ratio is less than 2.5:1. In an exemplary embodiment, the ratio is less than 1.5:1. It goes without saying that in addition to a parallel arrangement of the first instrument carrier and the second instrument carrier also an orientation in a fashion at least partially inclined with respect to one another may be envisaged so as to be able to effect even smaller effective distances in the region of the distal ends of the instruments.

According to a further embodiment of the manipulating apparatus, at least one instrument drive is provided with a position-controlled motor which is controlled in such a way that, when the instrument carrier is rotated about the longitudinal axis, the transmission port that is coupled with the instrument drive performs a local compensation movement so that a local rotation angle position of the transmission port with respect to the instrument carrier is maintained. When the instrument carrier is rotated, the instrument drives remain in their original position. In this way, the rotation of the instrument carrier mediately effects a rotation of the transmission ports when a movement coupling is present. However, the motors of the instrument drives may be suitably controlled in such a way so as to perform a compensation movement. From the view of the mounted instrument, apart from the (global) rotation, no changes at the actual movement state are present (internal instrument reference system). In other words, the rotation of the instrument carrier for instance has no effect on the state of a gripper at the instrument and/or an (instrument-side internal) pivot angle between components of the instrument.

According to an alternative embodiment of the manipulating apparatus, at least one instrument drive is provided with a low-detent-torque motor or a clutch, wherein at the output side of the transmission element (in some respect) self-locking is present so that when the instrument carrier is rotated about a longitudinal axis the transmission port that is coupled with or arranged to be coupled with the instrument drive maintains its local rotation angle position with respect to the instrument carrier. In other words, in accordance with this embodiment, the movement of the instrument carrier and as a result of the self-locking, in turn, a feedback towards the input-side (proximal) end of the instrument carrier and/or the instrument drive would be present.

According to a further, alternative embodiment, when the instrument carrier is rotated, an undesired feedback or parasitic movement and/or entrainment of the transmission elements may be avoided by an appropriate design of the gear stages for the respective degrees of freedom of movement of the instrument. Hence, when the gear stage at the input side of the transmission element effects a defined rotational movement of the transmission element when the instrument carrier is rotated, and when the transmission stage(s) that is/are provided at the output-side of the transmission element effects/effect a rotation movement of the same magnitude but of the opposite direction, the relative rotation orientation of the transmission port with respect to the instrument carrier and/or with respect to the mounted instrument is not changed.

According to a further embodiment of the manipulating apparatus, the at least one transmission port comprises a driving profile which is arranged to be coupled with a mating profile of an instrument-sided instrument input in a positive-locking fashion, wherein the driving profile comprises an orientation contour for facilitating assembling. In an exemplary embodiment, the orientation contour effects a radial and a rotatory pre-alignment between the transmission port and an instrument input assigned thereto. The radial pre-alignment takes place with respect to a radial set position with respect to the longitudinal axis of the instrument carrier. The rotatory pre-alignment takes place with respect to a rotation position of the instrument input and/or the transmission port itself. This means in other words that, in an exemplary embodiment, an actual rotation position of the instrument-sided instrument input is adapted to an actual rotation position of the transmission port assigned thereto.

Accordingly, the driving profile may comprise insertion chamfers and such like, however, further also ramps and similar inclined surfaces for defining the relative rotation orientation between the driving profile and the mating profile. The ramps may define a pitch which is lager than a pitch of the driving profile of the mating profile. For instance, the driving profile and/or the mating profile may be arranged as square profile, i.e. comprising a pitch of 90°. Accordingly, it may be envisaged that the orientation contour, for instance, comprises merely two ramps for rotatory pre-alignment which thus defines a pitch of 180°. In other words, the instrument input of the instrument may be coupled with the transmission port in only two rotation orientations. The motion transmission may be however performed at a plurality of surfaces, depending on the design of the driving profiles and the mating profile. However, it may also be envisaged that the instrument may be mounted in four rotation orientations, in analogy to the pitch of the driving profile and/or the mating profile, when only each second of the four instrument-sided mating surfaces contacts one of the ramps.

According to a refinement of this embodiment, the driving profile comprises a driving recess at the distal end of the transmission port, wherein in a frontal region of the driving profile, inclined offset surfaces are arranged that surround the driving recess. For instance, the driving profile may be arranged as square profile, Torx-profile, splined shaft profile, hexagon profile and in a similar fashion, wherein the mating profile at the side of the instrument input is arranged in corresponding fashion.

According to a further embodiment, the driving interface comprises a plurality of transmission ports which are arranged in the holding section, wherein at least some of the transmission ports are axially spaced from one another so that the instrument-sided instrument inputs that are assigned to the transmission ports, are successively coupled with the transmission ports when the instrument arm is mounted. This may significantly simplify the mounting of the instrument at the instrument carrier and, in certain embodiments, the locking.

According to a further embodiment which may be alternative or in addition, the instrument drive which is assigned to the at least one transmission port is arranged to drive the transmission port in a reciprocating fashion when the instrument arm is mounted so as to support the engagement of the driving profile and the mating profile. This procedure may also be referred to as "Jiggling". In an exemplary embodiment, a plurality of transmission ports is at least temporarily simultaneously driven in a reciprocating fashion by the instrument drives assigned thereto, wherein the drive involves different rotation speeds. Overall, an oscillating rotation movement and/or an approximate oscillating rotation movement may be present at the transmission ports. In an exemplary embodiment, oscillation speeds of the single transmission ports deviate from one another. This may shorten and simplify the "finding" of the counter element and overall the mounting and locking of the instrument arm at the instrument carrier. In this way, in an exemplary embodiment, account is taken of the fact that the mounting is generally conducted "blind" as no clear view to the mounting spot is present.

In respect of the manipulating system, the above described and other objects of the present disclosure are achieved by a manipulating system for minimally invasive surgical operations, for instance by a remote manipulating system for minimally invasive single-port-operations, that is provided with a control platform comprising a manipulating apparatus in accordance with one of the aspects described herein. In at least some embodiments, the control platform substantially consists of the manipulating apparatus. However, embodiments may be also envisaged, wherein in addition further modules are provided, for instance additional manipulating apparatuses, observation apparatuses, illumination apparatuses, supports for microscopes, endoscopes, exoscopes, and such like.

It is to be understood that the previously mentioned features and the features mentioned in the following may not only be used in a certain combination, but also in other combinations or as isolated features without leaving the spirit and scope of the present disclosure.

BRIEF DESCRIPTION OF THE DRAWINGS

Further features and advantages of the disclosure are disclosed by the following description of a plurality of exemplary embodiments, with reference to the drawings, wherein:

FIG. 1 is a schematic, greatly simplified perspective view of an operation environment including a remote manipulating system;

FIG. 2 is a detailed view of the illustration according to FIG. 1;

FIG. 10 is a broken partial view of the arrangement according to FIG. 9 in an orientation that corresponds to the orientation of the view according to FIG. 7;

FIG. 11 is a greatly simplified view of a longitudinal cross section through a transmission section of an instrument carrier, wherein the arrangement underlying FIG. 11 is at least similar to the arrangement according to FIG. 10;

FIG. 12 is a perspective enlarged view of a distribution section of an instrument carrier, wherein for illustrative purposes several components are omitted;

FIG. 13 is a further enlarged view of the arrangement according to FIG. 12 in a partially cross-sectional state in an orientation that deviates from FIG. 12;

FIG. 14 is an exemplary perspective rear partial view of components of a manipulating apparatus according to FIGS. 3 to 5 for elucidating a rotation drive;

FIG. 15 is an enlarged perspective view of an instrument carrier for elucidating an assembly, wherein components are omitted for illustrative purposes;

FIG. 18 is a further perspective partial view of the arrangement according to FIG. 17, wherein further components are omitted;

FIG. 19 is a proximal view of an arrangement of a transmission port having a driving profile;

FIG. 20 is a perspective view of the arrangement according to FIG. 19 for elucidating a driving recess; and FIG. 21 is an unwound view of a circular arrangement of a plurality of transmission ports which are axially displaced with respect to one another and which are arranged to be coupled with instrument inputs of an instrument.

DETAILED DESCRIPTION OF EXEMPLARY EMBODIMENTS

Figure 3:
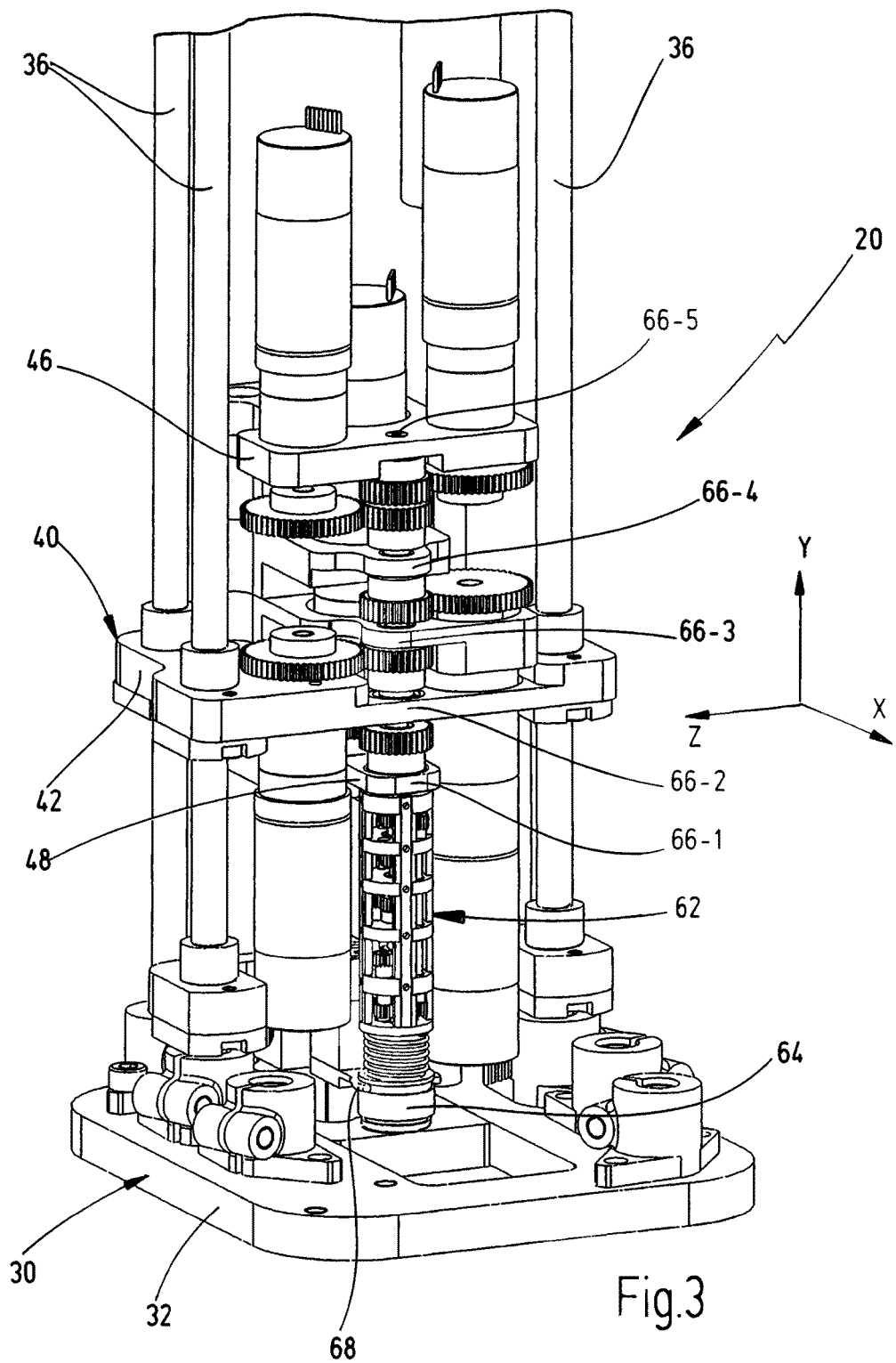
FIG. 3 is a perspective lateral partial view of a manipulating apparatus in accordance with at least some aspects of the present disclosure.

For explanatory purposes, in at least some of the figures described in the following a (Cartesian) coordinate system X-Y-Z is shown which shall be used hereinafter for illustrating defined directions and orientations. It goes without saying that the coordinate system X-Y-Z merely serves for illustrative and elucidative purposes and not to limit the scope of the disclosure. It further goes without saying that for describing the several embodiments and aspects of this disclosure also other coordinate systems including other orientations and attributions may be used. It is within the scope of the capability of the skilled person to apply respective (conceptual) transformations.

The same applies in the following also to direction indications and indications for spatial orientation, for instance top, bottom, lateral, front, rear, etc. Also the use of terms of that kind shall not be interpreted in a limiting sense. As long as terms of that kind are used in the context of distinct illustrations and orientations, they may refer to the actually shown illustration and thus replaced by respective modified attribution terms in modified views, associated with altered orientations and view directions.

In the following, a view which is oriented perpendicular to the X-direction is referred to as lateral view. Further, a view which is orientated perpendicular to the Z-direction is referred to as frontal (or rear) view. A view which is oriented perpendicular to the Y-axis is referred to as top view or bottom view.

FIG. 1 shows a perspective simplified view of an operation setting 10 which may also be referred to as remote medical operation system. In the operation setting 10 a manipulating system 12 is provided which is, so to say, provided between an operating surgeon that has been provided with a workplace 14 and a to-be-treated patient 16. The operating surgeon controls the manipulating system 12 via the workplace 14 by appropriate commands. The manipulating system 12 may also be referred to as robotic manipulator or as remote manipulating system. In the operation setting 10 the workplace 14 does not necessarily have to be placed immediately in the vicinity or adjacent to the manipulating system 12. Accordingly, also remote medical applications may be envisaged.

The manipulating system 12 which is in FIG. 1 merely shown in exemplary fashion comprises for instance a column arrangement and is assigned to a support (bench) for the patient 16. The manipulating system 12 comprises a control platform 18 which is arranged to be controlled via the workplace 14. The control platform 18 is arranged to hold and control at least one instrument 22, for instance a surgical instrument or a diagnostic instrument. To this end, the control platform 18 comprises at least one manipulating apparatus 20. In the following, exemplary embodiments of manipulating apparatuses 20 will be described.

FIG. 2 shows a greatly simplified detailed view of FIG. 1 in the region of a body opening of the patient 16 through which a minimally invasive procedure is performed. Further, two instruments 22 are indicated in FIG. 2 which respectively comprise an elongated shaft or arm 24. The body opening which may also be referred to as engagement spot is designated in the FIGS. 1 and 2 by 26. It is desired for minimally invasive procedures to use, if possible, only local engagement spots 26 having extensions as small as possible. For instance, in the FIGS. 1 and 2 a so-called single-port-operation is illustrated, wherein merely a single engagement spot (body opening) 26 is used. Through the single engagement spot 26, two instruments 22 are guided in the interior of the body of the patient 16. This poses huge challenges to the manipulating apparatus 20, as the instruments 22 are guided and driven in a fashion immediately adjacent to one another. In an exemplary embodiment, the instruments 22 are arranged to be moved and/or actuated independently of one another such a plurality of driving members is provided at the manipulating apparatus 20.

The instruments 22 themselves may be for instance arranged as endoscopic instruments, laparoscopic instruments, surgical instruments and such like. In this context, reference is made to US 2015/0119918 A1 which discloses embodiments of instruments 22 having a plurality of degrees of freedom of movement and/or degrees of freedom of actuation.

Figure 4:
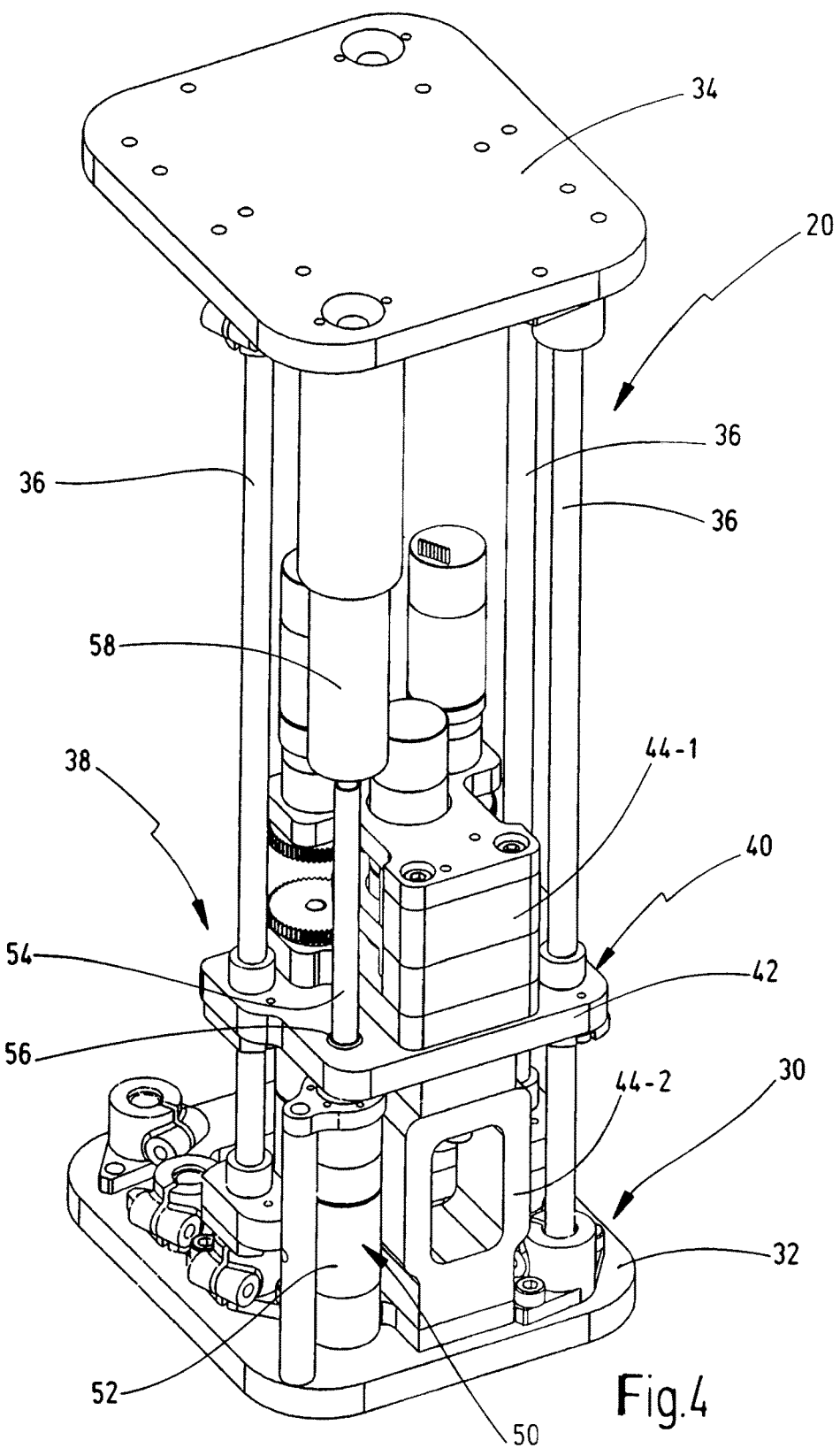
FIG. 4 is a further view of the manipulating apparatus according to FIG. 3 in a deviating orientation.
Figure 5:
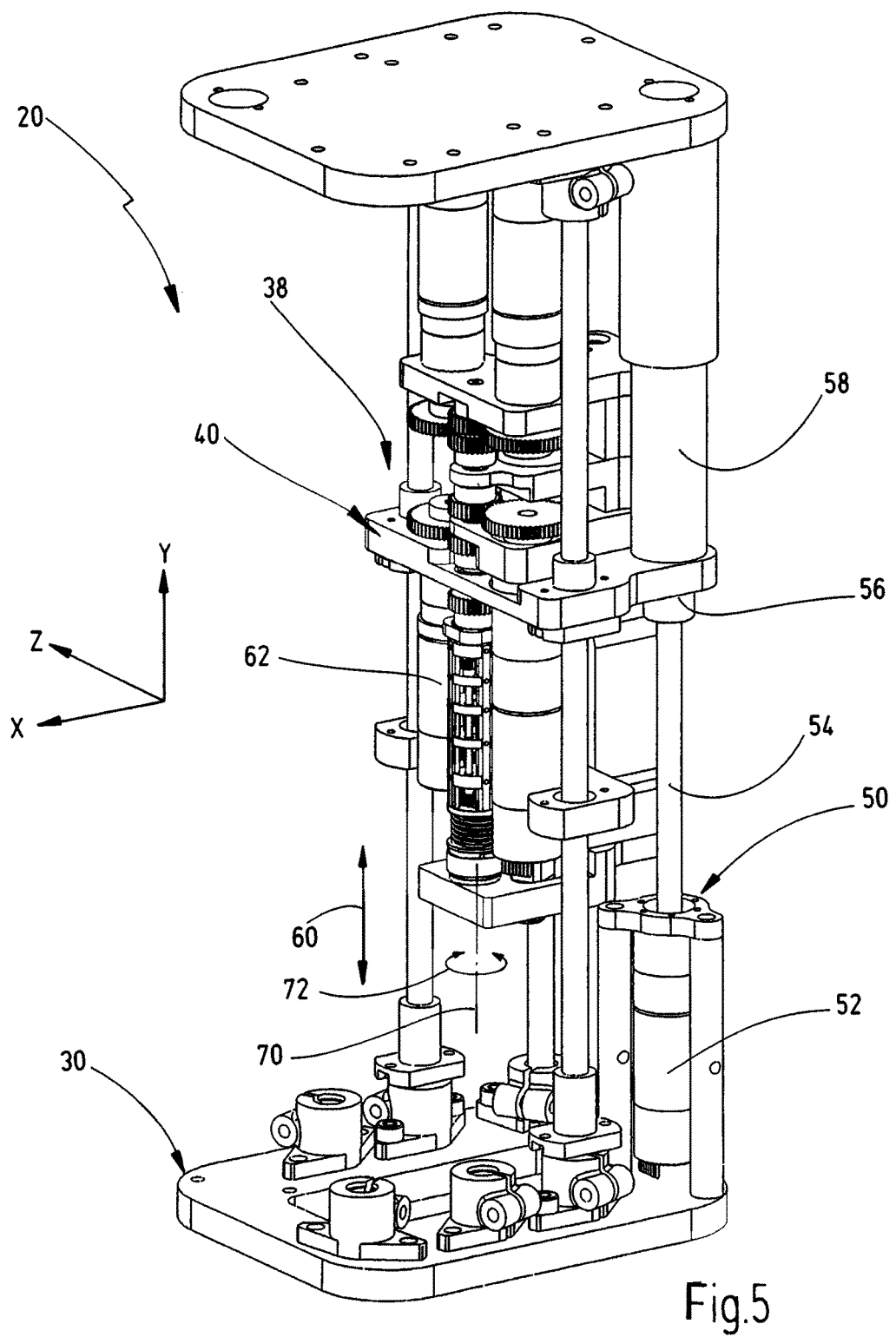
FIG. 5 is yet a further view of the manipulating apparatus according to FIG. 4 in a further perspective (frontal) orientation, wherein FIG. 5 elucidates a position of a carriage that deviates from the illustration according to FIGS. 3 and 4.

With reference to the FIGS. 3, 4 and 5 an exemplary arrangement of a manipulating apparatus 20 for instruments 22 is elucidated which may form a part of the manipulating system 12 and the operation setting 10. The manipulating apparatus 20 comprises a frame 30 which comprises, in accordance with the embodiment illustrated in the FIGS. 3 to 5, a base plate 32 and a base plate 34 that is opposite to the base plate 32. Guide columns 36 that define a longitudinal guide 38 extend between the base plates 32, 34. A carriage 40 is movably mounted to the longitudinal guide 38.

The longitudinal guide 38 enables a movement or displacement of the carriage 40 in a longitudinal direction (parallel to the Y-direction in the FIGS. 3 to 5). When reference is made within the context of this disclosure to a longitudinal direction or longitudinal movement, this shall be understood as the main extension direction of an arm or shaft 24 of an instrument 22 mounted to the manipulating apparatus 20. Depending on the global arrangement and orientation of the manipulating apparatus 20, the longitudinal direction may correspond to a (global) vertical direction, horizontal direction, lateral direction or a direction that is spatially obliquely oriented. According to the configuration of an operation setting 10 exemplarily shown in FIG. 1, the manipulating apparatus 20 is arranged to move instruments 22 "from the top" to the patient 16. Accordingly, the longitudinal direction (Y-direction) is aligned with the vertical direction. This shall be however not interpreted in a limiting sense.

The longitudinal guide 38 is in the FIGS. 3 to 5 arranged as a column guide. Other guide principles (trapezoid guide, etc.) may be envisaged. The carriage 40 is mounted to the guide column 36 in a fashion movable with respect thereto by bushings. The carriage 40 involves a carriage base 42 which is adjoined by a carriage frame 44, refer also to FIG. 4, wherein in FIG. 4 a first part of the carriage frame is indicated by 44-1 and a second part of the carriage frame is indicated by 44-2, wherein both parts 44-1, 44-2 extend from the carriage base 42 in opposite directions. The carriage 40 may also be referred to as slide. The carriage frame 44 exemplarily holds a first connection support 46 and a second connection support 48, refer also to FIG. 3. The connection supports 46 and 48 are displaced from the carriage base in the longitudinal direction (Y-direction) and serve for holding and/or for guiding further components of the manipulating apparatus 20.

With particular reference to the FIGS. 4 and 5, a longitudinal drive 50 is elucidated which may also be referred to as carriage drive. The longitudinal drive 50 is arranged to displace the carriage 40 and components attached thereto in the longitudinal direction Y, refer also to a double arrow designated by 60 in FIG. 5. The longitudinal drive 50 comprises a motor 52 that drives a spindle 54. The spindle 54 is coupled with a spindle nut 56 which is mounted to the carriage 40, for instance to the carriage base 42. The spindle nut 56 is mounted to the carriage 40 in a torque-proof fashion and movable with respect to and/or along the spindle 54. The spindle 54 and the spindle nut 56 may jointly form a screw spindle drive and/or a ball screw spindle drive. The motor 52 is mounted to the frame 30, for instance to the base plate 32. The motor 52 may drive the spindle 54 in a direct fashion or via an interposed transmission gear. The spindle 54 is, frame-sided, further guided in a spindle guide 58 which is mounted to the (upper) base plate 34. According to the embodiment of the longitudinal drive 50 elucidated with reference to FIGS. 4 and 5, the motor 52, the spindle 54 and the spindle guide 58 are arranged in series in a concentrical fashion. This arrangement requires a certain axial installation space (in the longitudinal direction).

The longitudinal drive 50 may in an alternative (not explicitly shown) embodiment mediately act on the spindle 54 and/or the screw spindle. It may also be envisaged to arrange the motor 52 in a fashion parallel to and offset from the spindle 54. To this end, between the motor 52 of the longitudinal drive 50 and the spindle 54, a transmission stage (for instance gear stage) may be provided. Accordingly, the longitudinal drive 50, for instance the motor 52 thereof, may be oriented parallel to the spindle 54 and require the same axial installation space as the spindle 54. This may overall lead to a reduced axial installation space need for the longitudinal drive 50.

At the carriage 40, for instance at the carriage base 42 thereof, further an instrument carrier 62 is mounted which is arranged for holding, guiding and controlling an instrument 22. To this end, the instrument carrier 62 comprises at its distal end a holding section 64 to which a proximal end of an instrument arm 24 may be mounted (refer also to FIG. 16). In the mounted state, the instrument arm 24 and the instrument carrier 62 are oriented in a fashion aligned with respect to one another. The instrument carrier 62 is mounted to the carriage 40 in a turnable and/or rotatable fashion. To this end, at least one bearing 66 is formed between the carriage 40 and the instrument carrier 62. In FIG. 3, several bearing spots which are mediately or immediately coupled with the instrument carrier 62 are designated by 66-1, 66-2, 66-3, 66-4 and 66-5. A direct bearing is present at the bearing spot 66-1. A mediate bearing of the instrument carrier 62 is present at the bearing spots 66-2 to 66-5 by means of which transmission elements 174 to 180 are mounted at the carriage 40 (refer also to FIG. 11). Further, a guide 68 which is exemplarily arranged as guide fork is assigned to the distal end of the instrument carrier. The guide 68 is mounted to the carriage 40 and engages a groove at the holding section 64.

In FIG. 5 a longitudinal axis of the instrument carrier 62 is indicated by 70. The instrument carrier 62 is movable together with the carriage 40 by the longitudinal drive 50 in the longitudinal direction (double arrow 60). Further, the instrument carrier 62 is, via the bearing 66, turnable and/or rotatable about the longitudinal axis 70, refer to a curved double arrow 72 in FIG. 5.

Figure 6:
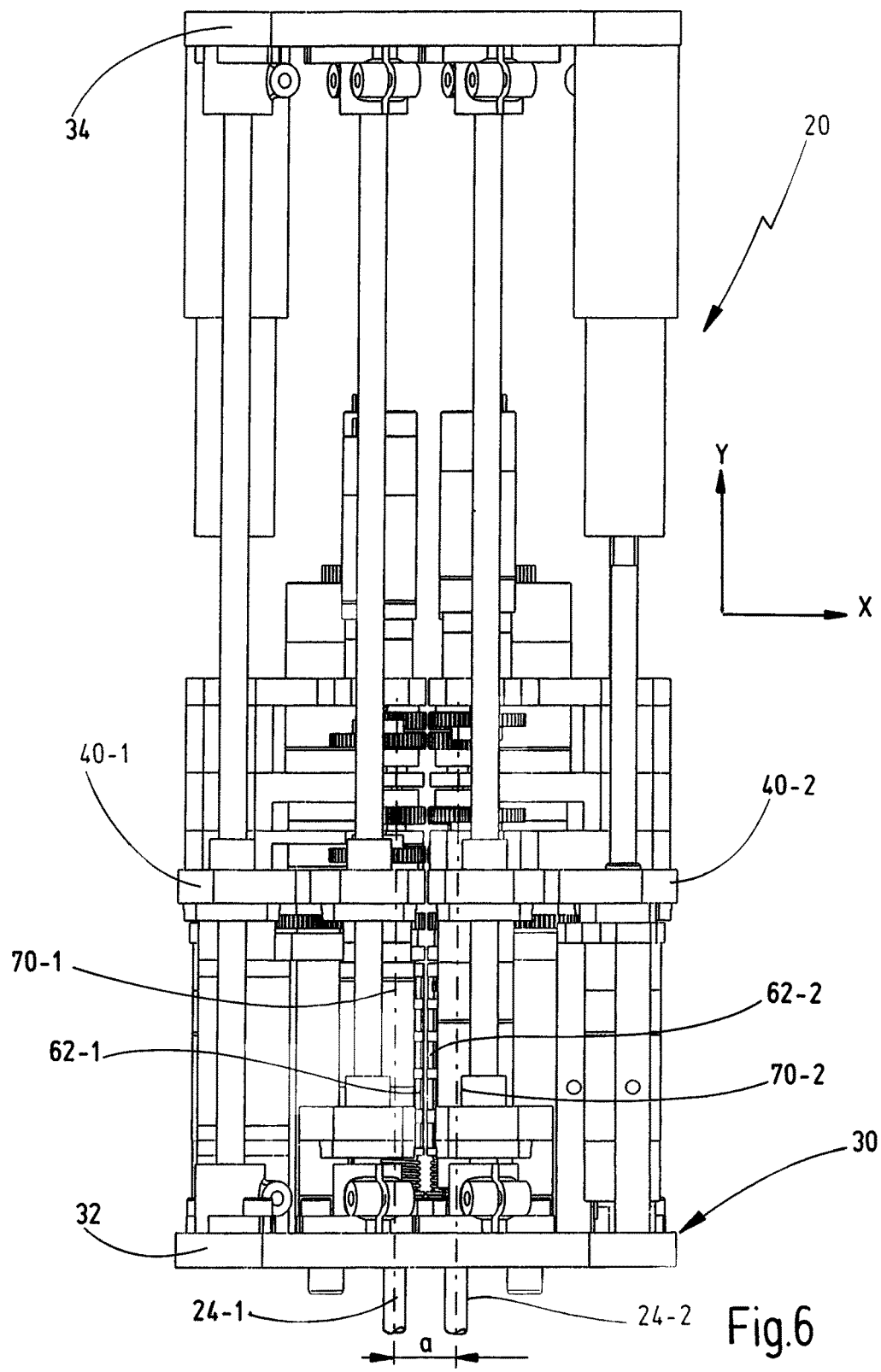
FIG. 6 is a schematic lateral view of a manipulating apparatus that is modified with respect to the illustration according to FIGS. 3 to 5, wherein the manipulating apparatus comprises a first instrument carrier for holding a first instrument and a second instrument carrier for holding a second instrument.

FIG. 6 shows a side view of a further embodiment of a manipulating apparatus 20 which has a base structure which basically corresponds to the manipulating apparatus 20 elucidated with reference to FIGS. 3, 4 and 5. However, at the manipulating apparatus 20 two carriages 40-1, 40-2 are mounted which are drivable in a fashion basically independently of one another, wherein the carriages 40-1, 40-2 respectively support an instrument carrier 62-1, 62-2 to which respectively an instrument arm 24-1, 24-2 is mounted. For instance, the manipulating apparatus 20 according to FIG. 6 comprises a mirrored configuration and/or an orientation turned by 180° between the carriages 40-1, 40-2 and the instrument carriers 62-1, 62-2. In the FIGS. 3, 4 and 5, for illustrative purposes, the respective second entity is not shown.

Figure 7:
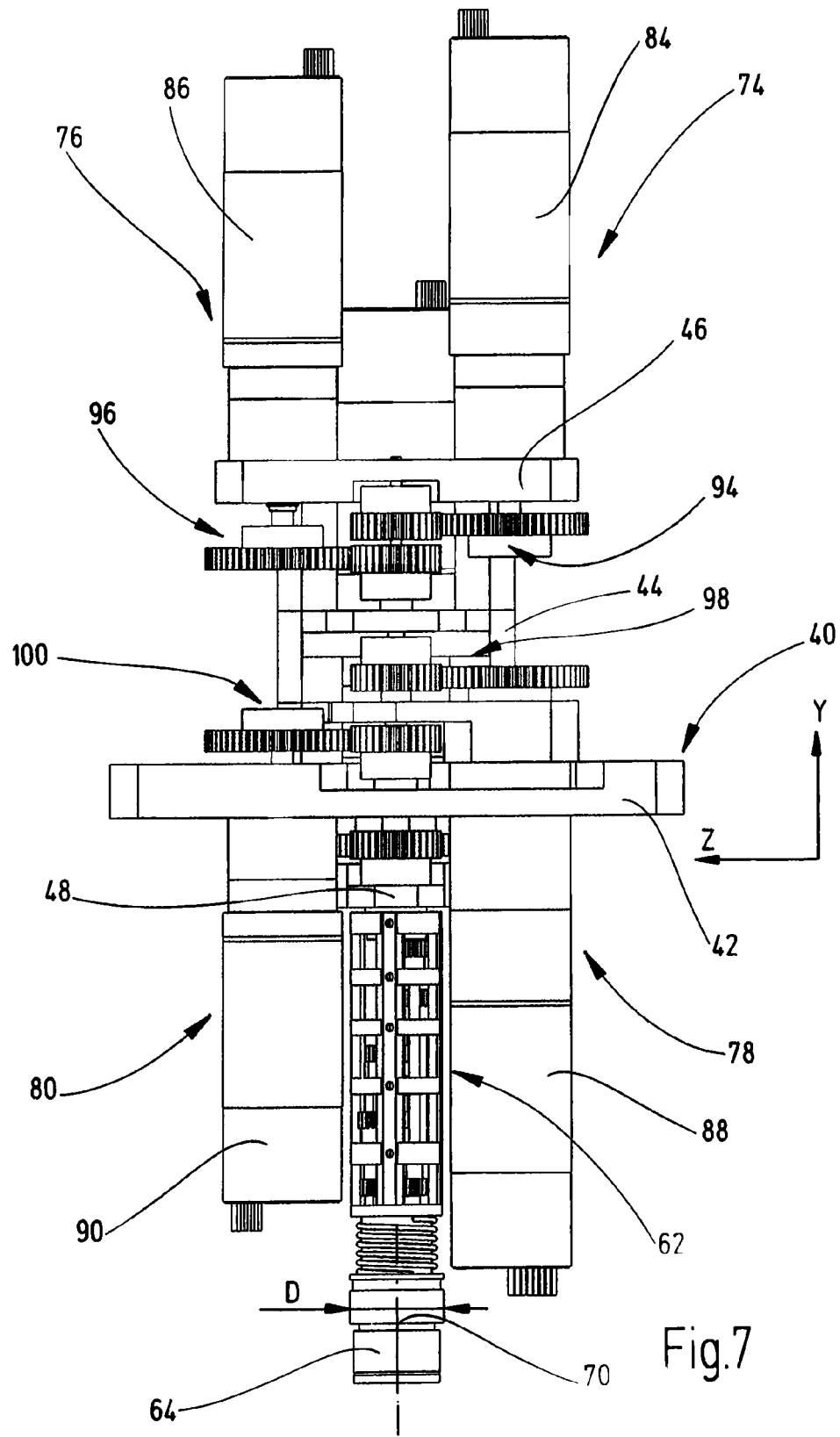
FIG. 7 is a lateral partial view of the arrangement according to FIG. 3 for elucidating instrument drives that are coupled with an instrument carrier.

It can be further seen from FIG. 6 that the instrument carriers 62-1, 62-2 are arranged in a fashion immediately adjacent and parallel to one another. This has the effect that longitudinal axis 70-1, 70-2 which are defined by the instrument carrier 62-1, 62-2 only have a small offset distance therebetween (distance in X-direction). This has the effect that also the instrument arms 24-1, 24-2 which are mounted to the instrument carriers 62-1, 62-2 may be arranged in close proximity with respect to one another. A distance between the longitudinal axis 70-1, 70-2 is indicated in FIG. 6 by a. An outer diameter of the instrument carrier 62 is indicated in FIG. 7 by D. In an exemplary embodiment, the configuration of the manipulating apparatus 20 allows for a very small ratio between the distance a and the diameter D (a/D or a:D). Several aspects of the configuration of the manipulating apparatus 20 enable the desired spatial proximity between the instrument carriers 62-1, 62-2 and instruments 22 attached thereto. This will be described in more detail hereinafter.

Figure 8:
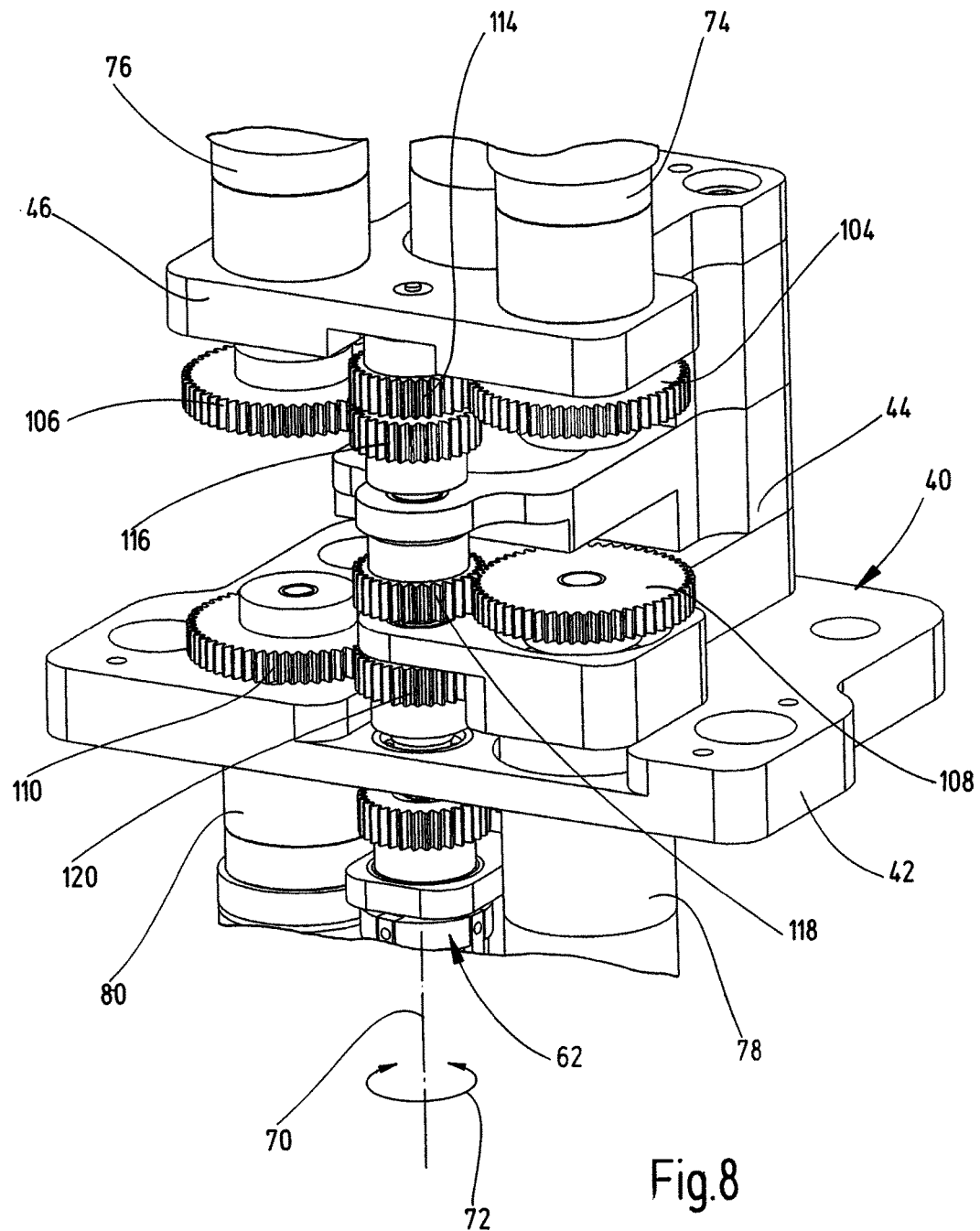
FIG. 8 is a cross-sectional perspective partial view of the arrangement according to FIG. 7 in an orientation that deviates from FIG. 7.

For a more detailed illustration of this embodiment, FIG. 7 shows a frontal view of the carriage 40. FIG. 8 shows a corresponding enlarged perspective partial view. At the carriage 40, an instrument carrier 62 is mounted in a fashion as basically already described herein. Further, at the carriage 40, instrument drives are mounted, for instance a first instrument drive 74, a second instrument drive 76, a third instrument drive 78, and a fourth instrument drive 80. The first instrument drive 74 comprises a first motor 84. The second instrument drive 76 comprises a second motor 86. The third instrument drive 78 comprises a third motor 88. The fourth instrument drive 80 comprises a fourth motor 90. The instrument drives 74, 76, 78, 80 are arranged to control degrees of freedom of movement and/or degrees of freedom of actuation on the side of a coupled instrument 22 so as to induce activities of the instrument 22.

The instrument drives 74, 76, 78, 80 are not arranged to drive the instrument carrier 62 itself. Rather, movements that are generated by the instrument drives 74, 76, 78, 80 are, so to say, transmitted through the instrument carrier 62 to the instrument 22 attached thereto. The instrument drives 74, 76, 78, 80 and the motors 84, 86, 88, 90 are oriented parallel to the longitudinal axis 70. The instrument drives 74 and 76 are mounted to the connection support 46 of the carriage 40. The instrument drives 78 and 80 are mounted to the carriage base 42 of the carriage 40. Overall, an approximately H-shaped configuration of the instrument drives 74, 76, 78, 80 is present, wherein the first instrument drive 74 and the second instrument drive 76 as well as the third instrument drive 78 and the fourth instrument drive 80 are respectively arranged at opposite sides of the longitudinal axis 70 of the instrument carrier 62. Different configurations may be envisaged.

For transmitting the driving motion to the instrument carrier 62 (and/or through the same), the first instrument drive 74 is coupled with a first input stage 94. The second instrument drive 76 is coupled with a second input stage 96. The third instrument drive 78 is coupled with a third input stage 98. The fourth instrument drive 80 is coupled with a fourth input stage 100. The input stages 94, 96, 98, 100 are coupled with the instrument carrier 62 at a proximal end thereof. The input stages 94, 96, 98, 100 are arranged as gear stages. The first input stage 94 comprises a first pinion 104 and a first gear 114. The second input stage 96 comprises a second pinion 106 and a second gear 116. The third input stage 98 comprises a third pinion 108 and a third gear 118. The fourth input stage 100 comprises a fourth pinion 110 and a fourth gear 120.

It goes without saying that also arrangements of instrument carriers 62 that comprise two, three or even more than four instrument drives 74, 76, 78, 80 are also covered by the scope of the present disclosure. By means of the instrument drives 74, 76, 78, 80 the gears 114, 116, 118, 120 assigned thereto may be rotated about a longitudinal axis 70. This, however, does not effect a rotation of the instrument carrier 62 as such around the longitudinal axis 70.

Figure 9:
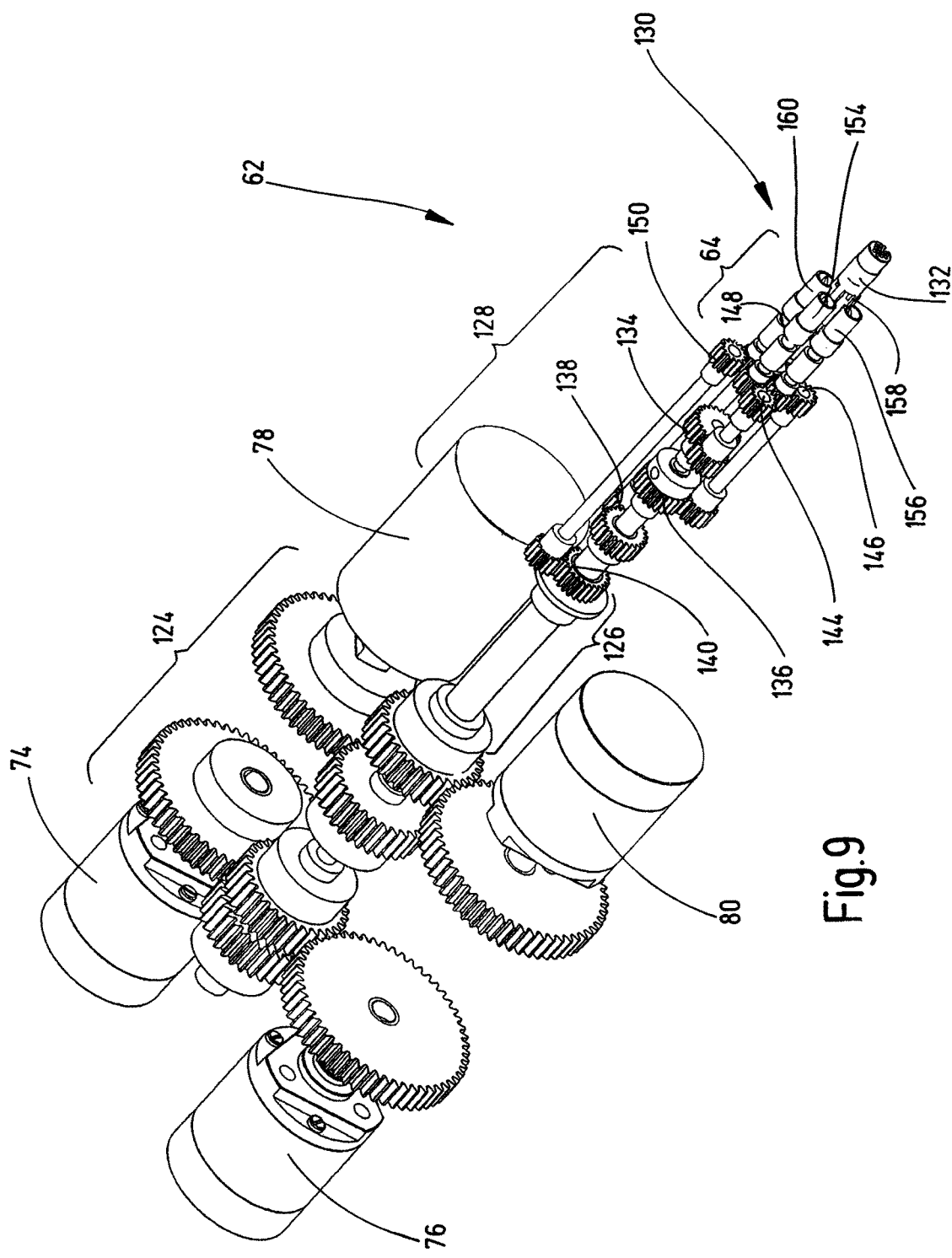
FIG. 9 is yet a further perspective illustration of the arrangement according to FIG. 7 in an orientation that deviates from FIG. 7, wherein for illustrative purposes further components are omitted.

FIG. 9 shows a perspective view of the arrangement according to the FIGS. 7 and 8, wherein for illustrative purposes, further components are omitted. The instrument carrier 62 comprises several sections. At the proximal end thereof, the instrument carrier 62 comprises an input section 124. In the region of the input section 124, the input stages 94, 96, 98, 100 are arranged. A transmission section 126 adjoins the input section 124. The transmission section 126 may also be referred to as concentrical transmission section. The transmission section 126 comprises a concentrical shaft arrangement (refer also to FIG. 11). A distribution section 128, in which the movements and/or torques that are transmitted via the transmission section 126 are output, adjoins the transmission section 126. A driving interface 130 that is assigned to the holding section 64 of the instrument carrier 62 adjoins the distribution section 128. Further, a contact interface 132 in a central region of the holding sections 64 is indicated in FIG. 9.

In the input section 124, movements and/or torques from the instrument drives 74, 76, 78, 80 that are arranged in an off-center fashion are transmitted to a concentric shaft arrangement in the transmission section 126. In the distribution section 128, in turn, a transmission of the movement and/or torque from the concentrical shaft arrangement to elements arranged in an off-center fashion takes place, namely to transmission ports 154, 156, 158, 160. To this end, the distribution section 128 comprises a first transition stage 134 that is coupled with a first output stage 144. Further, a second transition stage 136 is provided that is coupled with a second output stage 146. Further, a third transition stage 138 is provided that is coupled with a third output stage 148. Further, a fourth transition stage 140 is provided that is coupled with a fourth output stage 150. The first output stage 144 ends in the first transmission port 154. The second output stage 146 ends in the second transmission port 156. The third output stage 148 ends in the third transmission port 158. The fourth output stage 150 ends in the fourth transmission port 160.

The driving interface 130 involving the transmission ports 154, 156, 158, 160 serves for transmitting mechanical energy to the instrument 22, for instance for transmitting rotatory movements and/or torques. The contact interface 132 serves for transmitting electric energy and/or for transmitting electrical signals to instrument 22, and vice versa.

Overall, the embodiment of the instrument carrier 62 shown in FIG. 9 enables the transmission of four separate driving movements to the instrument 22. Those may also be referred to as degrees of freedom of movement for the instrument 22. A first transmission path for a first degree of freedom of movement extends from the first instrument drive 74 towards the first transmission port 154. A second path for a second degree of freedom of movement extends from the second instrument drive 76 towards the second transmission port 156. A third path for a third degree of freedom of movement extends from the third instrument drive 78 towards the third transmission port 158. A fourth path for a fourth degree of freedom of movement extends from the fourth instrument drive 80 towards the fourth transmission port 160. The arrangement provides four degrees of freedom of movement.

By means of an interposition of the concentrical transmission section 126, movements from the instrument drives 74, 76, 78, 80 that are arranged in an off-center fashion are transmitted to the transmission ports 154, 156, 158, 160 that are arranged in an off-center fashion, and in fact in a fashion basically independently of one another. The utilized movement paths and/or transmission paths use the same (geometrical) rotation axis in the region of the transmission section 126.

The arrangement of the instrument carrier 62 elucidated with reference to FIG. 9 may be further modified when the transition stages 134, 136, 138, 140 directly end in the transmission ports 154, 156, 158, 160. According to this embodiment, no (additional) output stages 144, 146, 148, 150 are necessary.

With reference to the FIGS. 10 and 11 which respectively illustrate broken, partial side views of the arrangement according to FIG. 9, the arrangement of the transmission section 126 and the sections (input section 124 and distribution section 128) adjoining the transmission section 126 will be elucidated in more detail. FIG. 11 shows a simplified, schematic longitudinal cross-section. In the input section 124, an input of the driving movements to the transmission section 126 takes place. In the distribution section 128, an output of the movements transferred by the transmission section 126 takes place. In the transmission section 126, a shaft arrangement is formed which may also be referred to as concentrical shaft arrangement 162. The shaft arrangement 162 involves transmission elements 174, 176, 178, 180, that couple input-sided gears 114, 116, 118, 120 with output-sided (distal) output pinions 164, 166, 168, 170.

A first transmission element 174 is exemplarily arranged as (central) shaft. A second transmission element 176 is arranged as tube or hollow shaft and surrounds the first transmission element 174. A third transmission element 178 is arranged as tube or hollow shaft and surrounds the second transmission element 176. A fourth transmission element 180 is arranged as tube or hollow shaft and surrounds the third transmission element 178. The first transmission element 174 connects the first gear 114 with the first output pinion 164. The second transmission element 176 connects the second gear 116 with the second output pinion 166. The third transmission element 178 connects the third gear 118 with the third output pinion 168. The fourth transmission element 180 connects the fourth gear 120 with the fourth output pinion 170. Accordingly, the transmission elements 174, 176, 178, 180 respectively connect the input stages 94, 96, 98, 100 assigned thereto with the corresponding output-sided transition stages 134, 136, 138, 140.

As a matter of principle, the first transmission element 174 involves the largest (axial) longitudinal extension. In descending order, the second transmission element 176, the third transmission element 178 and the fourth transmission element 180 follow. The transmission elements 174, 176, 178, 180 enable the transmission of control movements and/or driving torques to the instrument 22 through the instrument carrier 62, even though the instrument carrier 62 is mounted to the carriage 40 in a rotatable fashion.

With reference to FIGS. 12 and 13, the distribution section 128 of the instrument carrier 62 is elucidated in more detail. In the distribution section 128, the concentrically transmitted movements for the four degrees of freedom are transmitted through the transition stages 134, 136, 138, 140 along elements that are arranged in an off-center fashion with respect to the longitudinal axis towards the output stages 144, 146, 148, 150.

The first transition stage 134 involves a first peripheral gear 184 that is coupled with a first offset shaft 194, wherein at the distal end thereof a first offset pinion 204 is mounted that is assigned to the first output stage 144. The second transition stage 136 involves a second peripheral gear 186 that is coupled with a second offset shaft 196 that ends in a second offset pinion 206 that is assigned to the second output stage 146. The third transition stage 138 involves a third peripheral gear 188 that is coupled with a third offset shaft 198 that ends in a third offset pinion 208 that is assigned to the third output stage 148. The fourth transition stage 140 involves a fourth peripheral gear 190 that is coupled with a fourth offset shaft 200 that ends in a fourth offset pinion 210 that is assigned to the fourth output stage 150.

With reference to FIG. 13, it is apparent that the first output stage 144 further comprises a first offset gear 214 which is coupled with the first transmission port 154. The second output stage 146 further involves a second offset gear 216 which is coupled with the second transmission port 156. The third output stage 148 further involves a third offset gear 218 that is coupled with the third transmission port 158. The fourth output stage 150 further involves a fourth offset gear 220 that is coupled with the fourth transmission port 160.

In other words, at the output stages 144, 146, 148, 150 another off-center offset is present so as to reach the desired portions of the transmission ports 154, 156, 158, 160. Overall, the transmission ports 154, 156, 158, 160 are distributed about a longitudinal axis 70 of the instrument carrier 62 in a circular fashion. Is goes without saying that in at least some embodiments the last stage (output stage 144, 146, 148, 150) may be dispensed with when the transmission ports 154, 156, 158, 160 are directly coupled to the offset shafts 194, 196, 198, 200.

In an exemplary embodiment, the arrangement of the instrument carrier 62 and the instrument drives 74, 76, 78, 80 involves that the instrument carrier 62 may be turned or rotated about its longitudinal axis and, when this rotation movement takes place, the motors 84, 86, 88, 90 of the instrument drives 74, 76, 78, 80 do not have to be moved and/or pivoted at the same time. This may overall significantly minimize the installation space of the manipulating apparatus 20 and exemplarily enable an adjacent arrangement of two instrument carriers 62-1, 62-2 in closed proximity, refer also to FIG. 6.

With reference to FIG. 14, a rotation drive 224 for the instrument carrier 62 is elucidated in more detail. The rotation drive 224 enables a rotation of the instrument carrier 62 about its longitudinal axis 70, refer to the curved double arrow 72 in FIG. 14. The rotation drive 224 comprises a motor 226 that is mounted to the carriage 40, for instance to the carriage base 42. The motor 226 is coupled with the instrument carrier 62 via a gear stage 228 that involves a pinion 230 and a gear 232. The gear 232 is coupled with the holding section 64 and/or the driving interface 130 in a torque-proof fashion so as to be able to rotate an instrument arm 24 attached thereto together with the instrument carrier 62 about the longitudinal axis 70.

When the movement of the instrument carrier 62 takes place, the motors 84, 86, 88, 90 of the instrument drives 74, 76, 78, 80 remain at their original positions at the carriage 40. This may, under certain circumstances, lead to undesired parasitic output movements at the transmission ports 154, 156, 158, 160. To prevent these movements, the instrument drives 74, 76, 78, 80 may be controlled in an appropriate fashion so as to effect a defined counter movement to compensate the parasitic movement.

This may involve that the actual (overall) rotatory movements of the instrument carrier 62 with respect to the carriage 40 are calculated and/or measured so as to define appropriate counter movements at the level of the instrument drives 74, 76, 78, 80 to compensate the overall rotation (in view of the respective transmission port 154, 156, 158, 160). Hence, the motors 84, 86, 88, 90 may be operated accordingly. As a result, the mounted instrument 22 remains in a steady internal operation state, in spite of the overall rotation about the axis 70.

A further option for avoiding and/or compensating parasitic movements is to decouple the instrument drives 74, 76, 78, 80 and/or the input stages 94, 96, 98, 100 from the elements and/or components that are adjoining the distal end of the concentrical shaft arrangement 162. To this end, for instance a self-locking feature in the drive train may be used which has the effect that when the rotation of the instrument carrier 62 takes place, so to say, at the same time, a movement of the input stages 94, 96, 98, 100 and, as the case may be, the motors 84, 86, 88, 90 takes place. It may also be envisaged to decouple the motors 84, 86, 88, 90 in a deliberate fashion.

A further alternative option for compensating the parasitic movements is to design the involved gear stages in such a way that between the proximal input and the distal output of the instrument carrier a reversal of the direction but, however, a transmission of an equal (angular) amount of the rotation movement effected by the instrument drives 74, 76, 78, 80 at the transmission ports 154, 156, 158, 160 takes place.

Between the gear 232 and the holding section 64, the instrument carrier 62 comprises a rotation frame 236 which may also be referred to as cage. The rotation frame 236 effects a torque-proof connection between the gear 232 and the holding section 64 for driving the instrument arm 24. At the rotation frame 236, further the distribution section 128 and, at least partially, the driving interface 130 are mounted. Additionally, reference is made to FIG. 15 for the detailed configuration of the rotation frames 236. According to the embodiment elucidated with reference to FIGS. 14 and 15, the rotation frames 236 is arranged in a cage-like fashion and comprises an arrangement of bearing plates 238 that are axially spaced from one another and that are arranged in an approximately disc-like fashion. In the bearing plates 238, recesses are provided so as to receive and/or mount the elements that are involved in the motion transmission and/or force transmission. The bearing plates 238 of the rotation frames 236 are coupled with one another in a torque-proof fashion by a plurality of side bars 240. The side bars 240 are mounted to peripheral recesses of the bearing plates 238. The bearing plates 238 and the side bars 240 jointly form a cylinder cage. At the distal end of the rotation frames 236, an output flange 242 is coupled thereto. The output flange 242 is arranged for rotation drive of the mounted instrument arm 24.

Further, a locking receptacle 244 is mounted to the output flange 242. The locking receptacle 244 involves an axially displaceable locking sleeve 246 which is axially biased by a locking spring 248, refer also to the partial cross-sectional view of the holding section 64 in FIG. 16.

Figure 16:
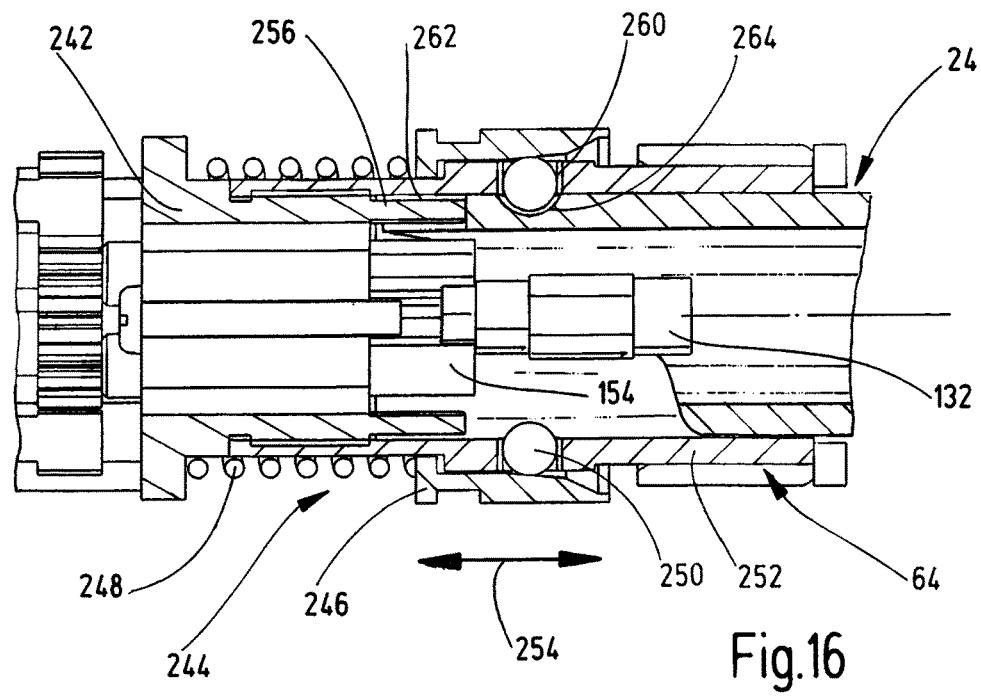
FIG. 16 is a partial cross-sectional view of a holding section of an instrument carrier to which an instrument arm is mounted.

The locking receptacle 244 further comprises a plurality of locking elements formed as locking balls 250 which are arranged to radially engage or disengage. The locking balls 250 are mounted in recesses of a holding bushing 252. This involves for instance a mounting in a ball seat 260 arranged in the form of a peripheral bore at the holding bushing 252, refer also to FIG. 17. The holding bushing 252 is coupled with the output flange 242. A movement direction of the locking sleeve 246 is indicated in FIG. 16 by a double arrow designated by 254. The locking sleeve 246 comprises an interior conical tapering such that the locking balls 250 may radially disengage when a movement of the locking sleeve 246 towards the proximal end of the instrument carrier 62 takes place.

In FIG. 16, further the instrument arm 24 of a mounted instrument 22 is sectionally indicated. The instrument arm 24 comprises a tubular end section in which at least one locking recess 264 in the form of a spherical recess or a circumferential groove is formed. The locking balls 250 may engage, in a locking state, the locking recesses 264 at the instrument arm 24. In this state, the locking balls 250 are retained by the conical inner surface of the locking sleeve 246. In an exemplary embodiment, the slope and/or tapering of the conical inner surface is such that in the engaged state self-locking is present between the locking sleeve 246 and the locking balls 250. In this way, the connection between the instrument carrier 62 and the instrument arm 24 is secured in a force-fit and/or frictionally engaged fashion. In addition, the locking spring 248 urges the locking sleeve 246 towards the locking state thereof. For releasing the locking connection, the locking sleeve 246 has to be deliberately moved, against the force of the locking spring 248, towards the proximal end of the instrument carrier 62 in such a way that the locking balls 250 may disengage from the locking recesses 264. Then, the instrument arm 24 may be released from the holding section 64. The locking sleeve 246 further comprises a groove which may be engaged by a guide 68 that is arranged as a guide fork may, refer also to FIG. 3. Via the groove, the locking sleeve 246 may be secured or actuated.

Figure 17:
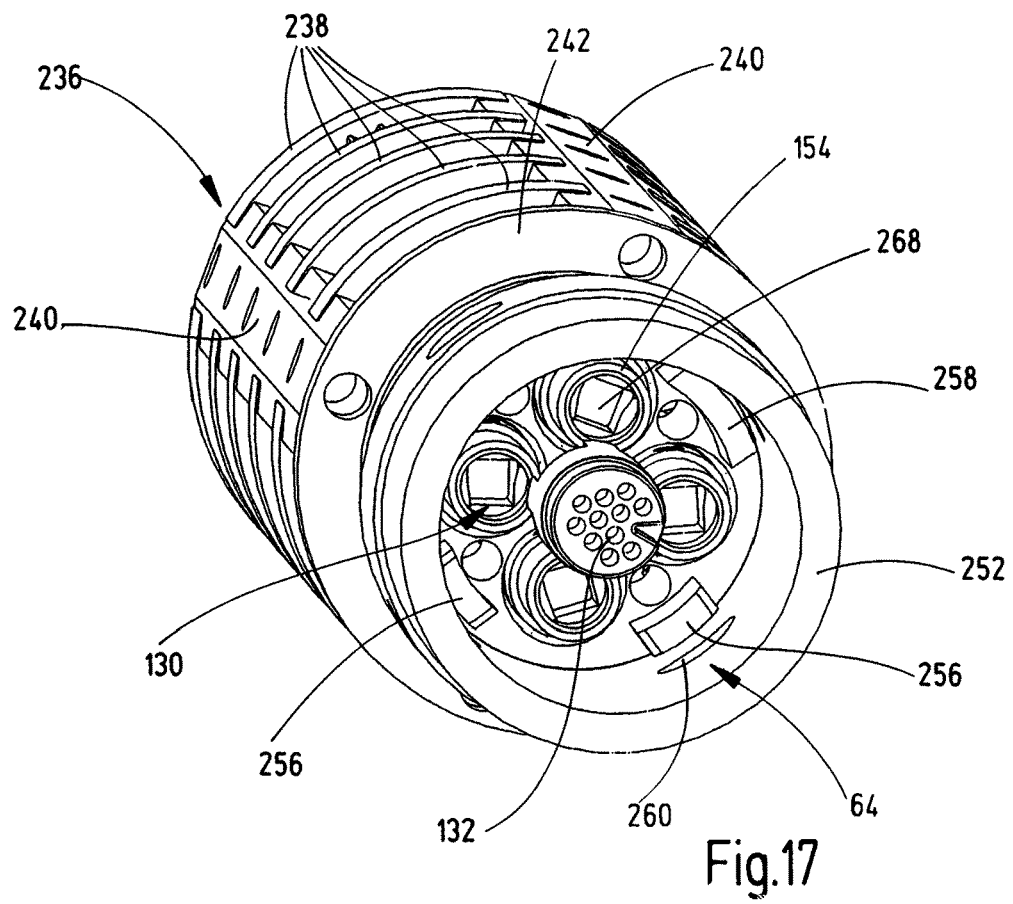
FIG. 17 is a perspective distal view of a holding section of an instrument carrier for elucidating a driving interface, wherein components are omitted for illustrative purposes.

Further, in the FIGS. 15, 16 and in FIG. 17, drivers 256 are indicated which are mounted at the output flange 242. The drivers 256 are arranged for rotation entrainment of the attached instrument 22. In addition to the drivers 256 there is further provided a rotational position securing element 258. The rotational position securing element 258 may be for instance arranged as an enlarged driver. The rotational position securing element 258 ensures that the instrument arm 24 may be mounted to the instrument carrier 62 only in a defined preferred orientation. The drivers 256 and/or the rotational position securing element 258 engage corresponding engagement recesses 262 at the instrument arm 24, refer also to FIG. 16. Further, in FIG. 17, an exemplary arrangement of the contact interface 132 is shown. The contact interface 132 provides a plurality of electric connections and/or contacts by means of which electric energy and/or electric signals may be transmitted. For instance, the contact interface 132 is arranged in a center of the holding section 64 and may be contacted by a respective counter element (plug and/or socket) on the side of the instrument 22.

At the transmission ports 154, 156, 158, 160, the driving interface 130 respectively comprises a driving profile 268 that is arranged for driving a mating profile 278 at an instrument-sided instrument input 276, refer particularly to FIGS. 17 to 21. The driving profile 268 exemplarily involves a driving recess 270. The driving profile 268 is for instance arranged as a square profile. Different arrangements of driving profiles may be envisaged. For facilitating the mounting procedure between the transmission ports 154, 156, 158, 160 and the instrument inputs 276, there is further provided an alignment contour 272 at the driving profile 268, refer to FIG. 19 and FIG. 20. The alignment contour 272 comprises inclined surfaces 274 that enable a radial alignment, but also a rotation position alignment between the transmission ports 154, 156, 158, 160 and the instrument inputs 276 (indicated in FIG. 21) assigned thereto.

By way of example, the instrument inputs 276 on the side of the instrument 22 comprise mating profiles 278 that are arranged to engage the driving profiles 268 and/or the driving recesses 270 thereof. The orientation contour 272 including the inclined surfaces 274 may contribute to the completion of a desired rotation position orientation between the elements. Also a radial offset between the coupling elements may be compensated by a respective insertion chamfer or insertion tapering.

FIG. 21 elucidates, with reference to an exemplary unwound illustration of an actually circular arrangement of transmission ports 154, 156, 158, 160, a further embodiment that facilitates the mounting of the instrument 22 to the instrument carrier 62. According to this exemplary embodiment, the respective transmission ports 154, 156, 158, 160 are somewhat axially displaced from one another so that the instrument inputs 276 on the side of the instrument 22 do not simultaneously, but successively engage the transmission ports 154, 156, 158, 160. A reverse orientation involving axially displaced instrument inputs 276 may be envisaged.

In this way, states may be avoided wherein some of the coupling pairs of transmission port and instrument input are not sufficiently accurate in their desired orientation. A further simplification of the mounting procedure may be effected by a targeted reciprocating pivot movement of the transmission ports 154, 156, 158, 160 by the instrument drives 74, 76, 78, 80 respectively assigned thereto. In this way, the transmission ports 154, 156, 158, 160 and the instrument inputs 276 may "find" and engage one another. In an exemplary embodiment, within the scope of this mounting procedure (also referred to as jiggling), the transmission ports 154, 156, 158, 160 are driven at different rotational velocities so that a variety of relative positions is present which increases the likelihood of a state in which all pairings are in the desired relative orientation.

What is claimed is:

1. A manipulating apparatus for instruments, the manipulating apparatus comprising:
   a frame,
   at least one instrument drive, and
   an instrument carrier that is movably mounted to the frame and comprises:
   a holding section arranged for holding an instrument arm of an instrument, and comprising a driving interface for transmitting mechanical energy to the instrument arm,
   at least one transmission port arranged at the driving interface, wherein the at least one instrument drive is operatively coupled with the at least one transmission port,
   a transmission section,
   at least one transmission element arranged in the transmission section and configured for motion transmission between the at least one instrument drive and the at least one transmission port,
   wherein the instrument carrier has a longitudinal axis and is at least sectionally rotatable about the longitudinal axis and relative to the frame,
   wherein the at least one transmission element is arranged concentrically with respect to the longitudinal axis,
   wherein the at least one transmission port is arranged off-center with respect to the longitudinal axis of the instrument carrier, and
   wherein a rotation of the instrument carrier about the longitudinal axis moves the at least one transmission port around the longitudinal axis of the instrument carrier.

2. The manipulating apparatus according to claim 1, wherein the driving interface comprises a first transmission port and a second transmission port that are radially displaced from the longitudinal axis and spaced from one another, wherein a first transmission element and a second transmission element are arranged in the transmission section, wherein a first instrument drive and a second instrument drive are provided, wherein a first freedom of movement degree and a second freedom of movement degree for a mounted instrument are provided, wherein the first instrument drive, the first transmission element, and the first transmission port are coupled with one another for rotation transmission and assigned to the first freedom of movement degree, wherein the second instrument drive, the second transmission element, and the second transmission port are coupled with one another for rotation transmission and assigned to the second freedom of movement degree, wherein the first transmission element and the second transmission element are arranged concentrically with respect to the longitudinal axis and drivable independently of one another, and wherein the second transmission element is tubular and at least sectionally surrounds the first transmission element.

3. The manipulating apparatus according to claim 2, wherein the driving interface comprises a third transmission port and a fourth transmission port that are radially displaced from the longitudinal axis and spaced from one another, wherein a third transmission element and a fourth transmission element are arranged in the transmission section, wherein a third instrument drive and a fourth instrument drive are provided, wherein a third freedom of movement degree and a fourth freedom of movement degree for the mounted instrument are provided, wherein the third instrument drive, the third transmission element, and the third transmission port are coupled with one another for rotation transmission and assigned to the third freedom of movement degree, wherein the fourth instrument drive, the fourth transmission element, and the fourth transmission port are coupled with one another for rotation transmission and assigned to the fourth freedom of movement degree, wherein the third transmission element and the fourth transmission element are arranged concentrically with respect to the longitudinal axis and drivable independently of one another, wherein the fourth transmission element is tubular and at least sectionally surrounds the third transmission element, and wherein the third transmission element is tubular and at least sectionally surrounds the second transmission element.

4. The manipulating apparatus as claimed in claim 2, wherein the first and second transmission ports are distributed about the longitudinal axis and mounted off-center with respect to the longitudinal axis to the instrument carrier.

5. The manipulating apparatus as claimed in claim 1, wherein the at least one transmission element is shaft-like or tubular and coupled with an input-side, proximal gear stage and an output-side, distal gear stage.

6. The manipulating apparatus as claimed in claim 1, wherein the at least one transmission element is, at a proximal end, coupled with the at least one instrument drive and, at a distal end, with the at least one transmission port, wherein, when the instrument carrier is rotated about the longitudinal axis, the respectively assigned instrument drive remains in its defined relative position with respect to the frame.

7. The manipulating apparatus as claimed in claim 1, wherein at least one longitudinal guide is formed at the frame, wherein a carriage that supports the instrument carrier is mounted to the at least one longitudinal guide, and wherein the instrument carrier and the carriage are jointly movable with respect to the frame.

8. The manipulating apparatus as claimed in claim 7, wherein the at least one instrument drive is mounted to the carriage.

9. The manipulating apparatus as claimed in claim 8, wherein a plurality of instrument drives is provided and mounted to the carriage, wherein the instrument drives are arranged at the carriage distributed about and offset from the instrument carrier, and wherein the instrument carrier is arranged in a boundary region of the carriage.

10. The manipulating apparatus as claimed in claim 7, further comprising a longitudinal drive, wherein the longitudinal drive comprises a motor that is attached to the frame and that drives a spindle that is coupled with the carriage.

11. The manipulating apparatus as claimed in claim 7, wherein the at least one instrument drive is mounted to the carriage and is arranged for rotating the instrument carrier about the longitudinal axis, wherein the rotation of the instrument carrier causes a circulation of the at least one transmission port about the longitudinal axis.

12. The manipulating apparatus as claimed in claim 1, wherein the holding section is arranged as a locking receptacle for a proximal end of an instrument, wherein the holding section comprises a plurality of locking elements that engage, in an engaged state, at least one locking recess at the instrument arm, and wherein the holding section comprises an axially displaceable locking sleeve that is arranged to be displaced against a biasing force for disengaging the locking elements from the engaged state.

13. The manipulating apparatus as claimed in claim 1, comprising a first instrument carrier and a second instrument carrier that are movably mounted to the frame and at least sectionally movable with respect to one another, wherein each instrument carrier is provided with a holding section for holding an instrument arm, wherein the first instrument carrier and the second instrument carrier are mounted to the frame parallel to and adjacent to one another.

14. The manipulating apparatus as claimed in claim 13, comprising a first carriage and a second carriage that is opposite to the first carriage, wherein the first instrument carrier is mounted to the first carriage and the second instrument carrier is mounted to the second carriage, wherein the first instrument carrier and the second instrument carrier are arranged in facing boundary regions of the first carriage and the second carriage, respectively.

15. The manipulating apparatus as claimed in claim 14, wherein longitudinal axes of the first instrument carrier and the second instrument carrier are spaced from one another at an offset dimension a having a ratio with an installation space diameter D of the instrument carrier which is less than 3.5:1.

16. The manipulating apparatus as claimed in claim 1, wherein the at least one instrument drive is provided with a position-controlled motor which is controlled in such a way that, when the instrument carrier is rotated about the longitudinal axis, the at least one transmission port that is coupled with the at least one instrument drive performs a local compensation movement about a longitudinal axis thereof such that a relative rotation angle position of the at least one transmission port with respect to the instrument carrier is maintained.

17. The manipulating apparatus as claimed in claim 1, wherein the at least one instrument drive is provided with a low-detent-torque motor or a clutch, wherein a self-locking feature is provided at an output-side of the at least one transmission element in such a way that, when the instrument carrier is rotated about the longitudinal axis, the at least one transmission port that is coupled with the at least one instrument drive maintains its relative rotation angle position with respect to the instrument carrier.

18. The manipulating apparatus as claimed in claim 1, wherein the at least one transmission port comprises a driving profile which is arranged to be coupled in a positive-locking fashion with a mating profile of an instrument-side instrument input, wherein the driving profile comprises a driving recess at a distal end of the transmission port, and wherein, in a frontal region of the driving profile, inclined offset surfaces are arranged that surround the driving recess and form an orientation contour.

19. The manipulating apparatus as claimed in claim 1, wherein the driving interface comprises a plurality of transmission ports that are arranged in the holding section, and wherein at least some of the transmission ports are axially offset from one another so that instrument-sided instrument inputs that are respectively assigned to the transmission ports are successively coupled with the transmission ports when the instrument arm is being mounted.

20. The manipulating apparatus as claimed in claim 1, wherein the driving interface comprises a plurality of transmission ports that are arranged in the holding section, and a plurality of instrument drives that are respectively assigned to the transmission ports, wherein the instrument drives are arranged to drive the transmission ports in a reciprocating fashion when the instrument arm is being mounted, wherein the transmission ports are simultaneously driven, and wherein the drive involves different reciprocating rotation speeds for the transmission ports.

21. A manipulating apparatus for instruments, the manipulating apparatus comprising:
   a frame,
   at least one instrument drive, and
   a first instrument carrier and a second instrument carrier that are movably mounted to the frame and at least sectionally movable with respect to one another, wherein the first instrument carrier and the second instrument carrier are mounted to the frame parallel to and adjacent to one another, and wherein each instrument carrier comprises:
   a holding section arranged for holding an instrument arm of an instrument, and comprising a driving interface for transmitting mechanical energy to the instrument arm,
   at least one transmission port arranged at the driving interface, wherein the at least one instrument drive is operatively coupled with the at least one transmission port, a transmission section,
at least one transmission element arranged in the transmission section and configured for motion transmission between the at least one instrument drive and the at least one transmission port,
wherein the first and second instrument carriers are at least sectionally rotatable about a longitudinal axis thereof,
wherein the at least one transmission element is arranged concentrically with respect to the longitudinal axis, and
wherein the at least one transmission port is arranged off-center with respect to the longitudinal axis, the manipulating apparatus further comprising:
a first carriage and a second carriage that is opposite to the first carriage, wherein the first instrument carrier is mounted to the first carriage and the second instrument carrier is mounted to the second carriage, and wherein the first instrument carrier and the second instrument carrier are arranged in facing boundary regions of the first carriage and the second carriage, respectively.

22. A robotic manipulating apparatus for instruments, the manipulating apparatus comprising:
a frame,
a first instrument drive and a second instrument drive, and
an instrument carrier that is movably mounted to the frame and comprises:
a holding section arranged for holding an instrument arm of an instrument, and comprising a driving interface for transmitting mechanical energy to the instrument arm,
a first transmission port and a second transmission port arranged at the driving interface, wherein the first instrument drive is operatively coupled with the first transmission port, wherein the second instrument drive is operatively coupled with the second transmission port, and wherein the first transmission port and the second transmission port are arranged off-center with respect to the longitudinal axis of the instrument carrier and spaced from one another,
a transmission section,
a first transmission element and a second transmission element arranged in the transmission section and configured for motion transmission between the two instrument drives and the two transmission ports,
wherein the instrument carrier is at least sectionally rotatable about a longitudinal axis thereof, and relative to the frame,
wherein the first transmission element and the second transmission element are arranged concentrically with respect to the longitudinal axis and drivable independently of one another,
wherein the second transmission element is tubular and at least sectionally surrounds the first transmission element, and
wherein a first freedom of movement degree and a second freedom of movement degree for a mounted instrument are provided by the manipulating apparatus,
wherein the first instrument drive, the first transmission element, and the first transmission port are coupled with one another for rotation transmission and assigned to the first freedom of movement degree,
wherein the second instrument drive, the second transmission element, and the second transmission port are coupled with one another for rotation transmission and assigned to the second freedom of movement degree, and
wherein a rotation of the instrument carrier about the longitudinal axis and relative to the frame causes a circular motion of the first transmission port and the second transmission port about the longitudinal axis.

\* \* \* \* \*